(12) United States Patent
Azpiroz et al.

(10) Patent No.: US 10,444,184 B2
(45) Date of Patent: Oct. 15, 2019

(54) OPERATION OF DIAGNOSTIC DEVICES INVOLVING MICROCHANNELS AND ELECTRODES

(71) Applicant: International Business Machines Corporation, Armonk, NY (US)

(72) Inventors: Jaione T. Azpiroz, Rio de Janeiro (BR); Emmanuel Delamarche, Thalwil (CH); Claudius Feger, Rio de Janeiro (BR); Ricardo L. Ohta, Sao Paulo (BR); Mathias B. Steiner, Rio de Janeiro (BR); Yuksel Temiz, Zug (CH)

(73) Assignee: International Business Machines Corporation, Armonk, NY (US)

( * ) Notice: Subject to any disclaimer, the term of this patent is extended or adjusted under 35 U.S.C. 154(b) by 403 days.

(21) Appl. No.: 15/199,529

(22) Filed: Jun. 30, 2016

(65) Prior Publication Data

US 2017/0184545 A1    Jun. 29, 2017

Related U.S. Application Data

(60) Provisional application No. 62/271,732, filed on Dec. 28, 2015.

(51) Int. Cl.

| | |
|---|---|
| *G01N 27/447* | (2006.01) |
| *B01L 3/00* | (2006.01) |
| *B01L 9/00* | (2006.01) |

(52) U.S. Cl.
CPC .... *G01N 27/44791* (2013.01); *B01L 3/50273* (2013.01); *B01L 3/502715* (2013.01);
(Continued)

(58) Field of Classification Search
CPC ....... G01N 27/44791; G01N 27/44756; G01N 27/44721; B01L 3/50273; B01L 9/50;
(Continued)

(56) References Cited

U.S. PATENT DOCUMENTS

| | | |
|---|---|---|
| 5,666,417 A | 9/1997 | Liang et al. |
| 5,955,028 A | 9/1999 | Chow |

(Continued)

FOREIGN PATENT DOCUMENTS

| | | |
|---|---|---|
| GB | 2422796 | 8/2006 |
| WO | WO2002061400 | 1/2002 |

(Continued)

OTHER PUBLICATIONS

Dietrich Kohlheyer et al., "Bubble-Free Operation of a Microfluidic Free-Flow Electrophoresis Chip with Integrated Pt Electrodes". MESA+ Institute for Nanotechnology, University of Twente, 2008 American Chemical Society Analytical Chemistry, vol. 80, No. 11, Jun. 1, 2008. pp. 4111-4118.

(Continued)

*Primary Examiner* — Dennis White
(74) *Attorney, Agent, or Firm* — Joseph Petrokaitis; Otterstedt, Wallace & Kammer, LLP

(57) ABSTRACT

An assembly is provided for interfacing with a microfluidic chip having at least one microscopic channel configured to receive a liquid sample for analysis. The assembly includes a chip carrier, an electronics module, an optical module, and a mechanical module. The chip carrier includes a base and a cover defining a cavity to receive the microfluidic chip. The electronics module includes a signal generator which applies at least one electrokinetic signal electrode(s) of the chip. The optical module includes an excitation radiation source which causes excitation radiation to impinge on the sample, and an emission radiation detector which detects radiation emitted from the sample. The mechanical module includes a chip-carrier receiving structure, relatable with respect to the optical module for focus and at least one degree of translational freedom.

17 Claims, 33 Drawing Sheets

(52) U.S. Cl.
CPC ............. *B01L 9/50* (2013.01); *B01L 9/527* (2013.01); *G01N 27/44721* (2013.01); *G01N 27/44756* (2013.01); *B01L 2200/027* (2013.01); *B01L 2300/023* (2013.01); *B01L 2300/041* (2013.01); *B01L 2300/0609* (2013.01); *B01L 2300/0645* (2013.01); *B01L 2300/0654* (2013.01); *B01L 2300/0816* (2013.01); *B01L 2400/0406* (2013.01); *B01L 2400/0424* (2013.01)

(58) Field of Classification Search
CPC .............. B01L 9/527; B01L 3/502715; B01L 2300/023; B01L 2300/0654; B01L 2400/0406; B01L 2200/027; B01L 2300/0645; B01L 2300/041; B01L 2300/0816; B01L 2300/0609; B01L 2400/0424

See application file for complete search history.

(56) References Cited

U.S. PATENT DOCUMENTS

| | | | |
|---|---|---|---|
| 7,011,793 | B2 | 3/2006 | Zhou |
| 8,795,523 | B2 | 8/2014 | Su et al. |
| 2002/0192112 | A1 | 12/2002 | Chow |
| 2003/0021725 | A1* | 1/2003 | Unno .................. B01L 3/5027 422/50 |
| 2008/0144028 | A1 | 6/2008 | Gruler |
| 2013/0209991 | A1 | 8/2013 | Wang |
| 2014/0038222 | A1 | 2/2014 | Alt et al. |
| 2014/0134748 | A1 | 5/2014 | Liu et al. |
| 2014/0199713 | A1 | 7/2014 | Quake et al. |
| 2014/0211204 | A1 | 7/2014 | Stedtfeld |
| 2014/0287527 | A1 | 9/2014 | Xiao |
| 2014/0342470 | A1 | 11/2014 | Su et al. |
| 2015/0056099 | A1 | 2/2015 | Peeters |

FOREIGN PATENT DOCUMENTS

| | | |
|---|---|---|
| WO | WO2006092317 | 9/2006 |
| WO | WO2014047737 A1 | 4/2014 |
| WO | WO2014070935 A1 | 5/2014 |
| WO | WO2014207618 A1 | 12/2014 |
| WO | WO2016094507 A2 | 6/2016 |

OTHER PUBLICATIONS

Dietrich Kohlheyer, "Microfluidic Free-Flow Electrophoresis for Proteomics-On-A-Chip". MESA+, Institute for Nanotechnology, University of Twente, 2008. pp. 1-199.

Christian Møller Pedersen, "Cell Sorting Using AC Dielectrophoresis, Christian Møller Pedersen". MIC { Department of Micro and Nanotechnology Technical University of Denmark, Feb. 6, 2006. pp. 1-99.

Franzblau, Michael, "Portable Microfluidic Fluid Handling System for the Detection of Protein Biomarkers in Whole Human Blood" (2014). Open Access Master's Theses. Paper 458, pp. 1-222, University of Rhode Island.

Jaione Tirapu Azpiroz et al., Microchannel, Microfluidic Chip and Method for Processing Viicroparticles in a Fluid Flow , unpublished U.S. Appl. No. 14/797,168, filed Jul. 12, 2015, pp. 1-30 plus 12 sheets drawings.

Jaione Tirapu Azpiroz et al., Trapping at Least One Microparticle , unpublished U.S. Appl. No. 14/797,170, filed Jul. 12, 2015, pp. 1-23 plus 7 sheets drawings.

Cholesterol testing on a smartphone Vlad Oncescu, Matthew Mancuso and David Erickson. Lab Chip, 2014,14, 759-763.

Alere Triage Products for Rapid Point of Care Diagnostics, pp. 1-6, downloaded from http://www.alere.com/en/home/productsservices/brands/triage.html, Jun. 30, 2016.

ESEQuant Lateral Flow Reader, pp. 1-3, downloaded from https://www.qiagen.com/bz/about-us/contact/oem-services/ese-instruments/esequant-lateral-flow-reader/, Jun. 30, 2016.

C. Faulstich, K. Haberstroh, R. Gruler, M. Eberhard, T. Wiest, D. Lentzsch, "Handheld and portable test systems for immunodiagnostics, nucleic acid detection and more" Proc. of SPIE vol. 6945, 69450H, Apr. 15, 2008, abstract only pp. 1-2.

Biotek FLx800 Fluorescence Reader, downloaded from http://www.biotek.com/products/microplate_detection/flx800_fluorescence_microplate_reader.html, Jun. 30, 2016, pp. 1-2.

Proteomic Profiling—represents the insights of Zeptosens technology, don loaded from http://www.bayertechnology.com/solutions/technologydevelopment/proteomicprofiling.html?option=com_content&task=view&id=21&Itemid=36 Jun. 30, 2016, p. 1.

Hongying Zhu et al., Optofluidic Fluorescent Imaging Cytometry on a Cell Phone, Anal Chem. Sep. 1, 2011; 83(17): 6641-6647.

Holomic Introduces a Cellphone-Based Rapid Test Reader at AACC 2012, downloaded from http://www.cellmic.com/content/recent-news/holomic-introduces-a-cellphone-based-rapid-test-reader-at-aacc-2012/ Jun. 30, 2016 pp. 1-3.

Mobile Phone Based Clinical Microscopy for Global Health Applications David N. Breslauer et. al. PLoS ONE, vol. 4, issue 7, p:e6320 (2009) pp. 1-7.

Qingshan Wei et al., "Fluorescent Imaging of Single Nanoparticles and Viruses on a Smart Phone" ACS Nano. Oct. 22, 2013; 7(10): p. 9147-9155.

Tassaneewan Laksanasopin et. al, A smartphone dongle for diagnosis of infectious diseases at the point of care. Sci Transl Med Feb. 4, 2015. vol. 7, Issue 273, p. 273re1. Sci. Transl. Med. pp. 1-11.

United Kingdom Intellectual Property Office, Combined Search and Examination Report, dated Jun. 22, 2017, pp. 1-7, corresponding British Patent Application GB1621803.4.

* cited by examiner

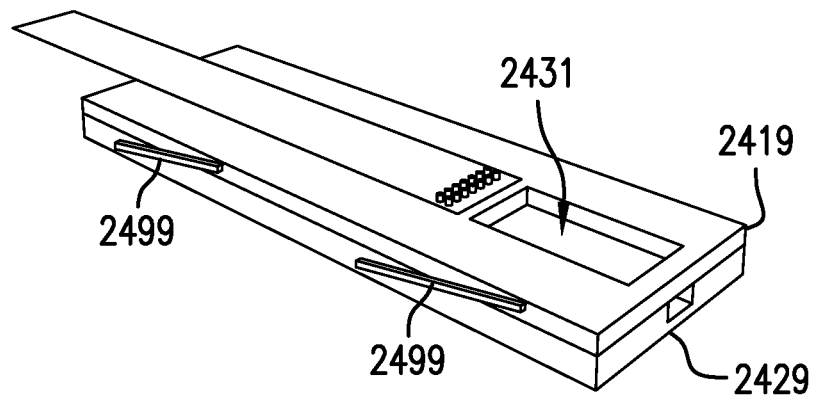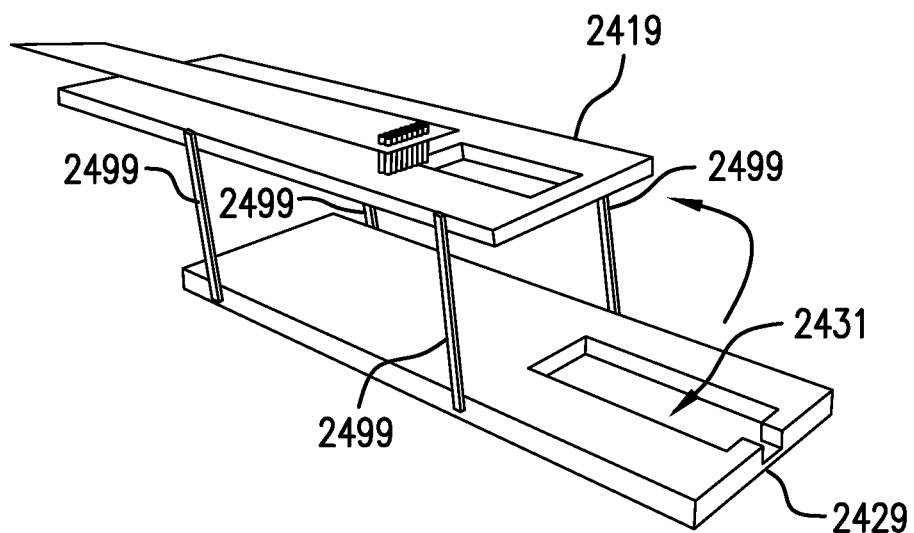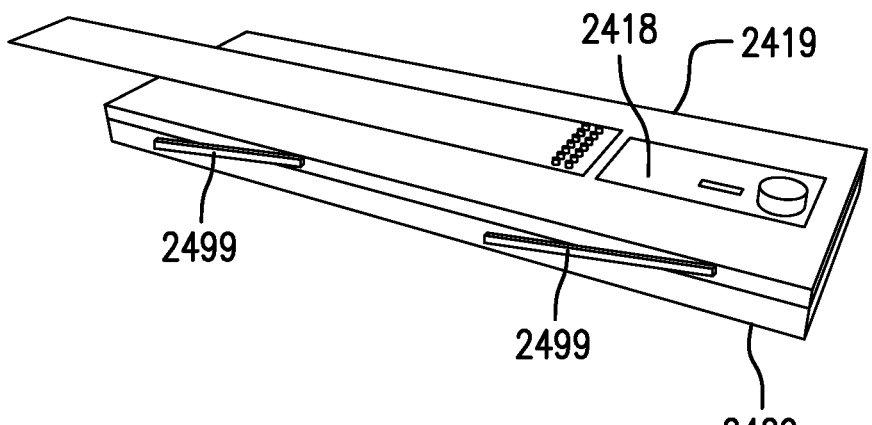
FIG. 24

OPERATION OF DIAGNOSTIC DEVICES INVOLVING MICROCHANNELS AND ELECTRODES

CROSS-REFERENCE TO RELATED APPLICATIONS

This application claims the benefit of U.S. Provisional Application 62/271,732 filed Dec. 28, 2015, the complete disclosure of which is expressly incorporated by reference herein in its entirety for all purposes.

STATEMENT OF GOVERNMENT RIGHTS

Not Applicable.

FIELD OF THE INVENTION

The present invention relates to the electrical, electronic and computer arts, and, more particularly, to healthcare and/or environmental solutions and the like.

BACKGROUND OF THE INVENTION

There has been a rapid increase in microfluidics-based Point-of-Care (PoC) devices, with potential as miniaturized laboratory platforms. Microfluidic devices typically have one or several microchannels. By including electrodes in microchannels, it is possible to apply electrical fields in a volume element of a liquid. This enables electrochemical detection of analytes, electroosmotic flow, dielectrophoresis (DEP) of particles or cells in microchannels, electrophoretic separation of particles and molecules, local heating, electrochemiluminescence, etc.

DEP is particularly interesting because it can generate a force by polarizing a suspended dielectric particle within a non-homogeneous electric field. Particle or cell manipulation via DEP therefore requires creating an electric field gradient, which is commonly done using planar metallic electrodes integrated or in close proximity to the microfluidic channel. Such electrode arrays are typically powered by applying alternating (AC) electric fields in the range of dozens of kHz up to hundreds of MHz. For this, the microfluidic device also needs to have two or more contact areas for powering the electrodes using a wave generator.

Fluorescence-based assays are widely used for detecting analytes. Fluorescence markers require optical detection with very sharp filters for the efficient separation between excitation light and fluorescent emission (usually, the fluorescence dyes have relatively small Stokes shift, of about 50 nm).

There are two known solutions:
1) Fluorescence microscopes+electronic laboratory bench signal generator: Very expensive and bulky setup equipment, not suitable for low cost point-of-care (PoC) applications (>$50 k) and also demands a laboratory infrastructure, but provides a high quality fluorescence analysis, using high quality light source, high quality filters and beam splitters, and can be equipped with very high sensitivity and low noise cameras with Peltier cooling, which obtains super high resolution fluorescence images and videos.
2) Lower cost and portable optical measurement devices or readers with miniaturized fluorescence optical detection system (LED illumination, focusing lens, dichroic mirror and photodetector), but these solutions are appropriate only for cellulose or paper strips (i.e. lateral flow assays) and do not have embedded signal generators for DEP signal generation. Although cheaper than a Fluorescence Microscope, will still cost several thousands of dollars (typically $8K-10K).

SUMMARY OF THE INVENTION

Principles of the invention provide techniques for diagnostic devices involving microchannels and electrodes and/or their operation. In one aspect, an exemplary assembly is provided for interfacing with a microfluidic chip having at least one microscopic channel configured to receive a liquid sample for analysis, at least one electrode embedded in the channel, and at least one chip contact coupled to the at least one embedded electrode. The assembly includes a chip carrier, in turn including a base; a cover, cooperatively defining, with the base, a cavity configured and dimensioned to receive the microfluidic chip; and at least one chip carrier contact to engage the at least one chip contact. The cover is attachable to the base, to secure the microfluidic chip in the cavity of the base. The cover has an aperture to permit the microscopic channel of the microfluidic chip to receive the sample for analysis and to permit passage of excitation and emission radiation. The assembly also includes an electronics module, in turn including at least one electronics module contact that engages the at least one chip carrier contact; and a signal generator, coupled to the at least one electronics module contact, which applies at least one electrokinetic signal to the at least one embedded electrode. The assembly even further includes an optical module, in turn including an excitation radiation source which causes excitation radiation to impinge on the sample through the aperture; and an emission radiation detector which detects radiation emitted from the sample through the aperture. Still further, the assembly includes a mechanical module including a chipcarrier receiving structure, relatable with respect to the optical module for focus and at least one degree of translational freedom. The mechanical module is electrically coupled to the electronics module. The focus and the at least one degree of translational freedom are controlled by the electronics module via the electrical coupling.

In another aspect, an exemplary method is provided for carrying out a test on a microfluidic chip having at least one microscopic channel configured to receive a liquid sample for analysis, at least one analytic electrode embedded in the channel, a plurality of liquid-presence-sensing electrodes embedded in the channel, and a plurality of chip contacts coupled to the at least one analytic electrode and the plurality of liquid-presence-sensing electrodes. The method includes detecting loading of the liquid sample, on a first such microfluidic chip, based on an impedance change at a first one of the liquid-presence-sensing electrodes; responsive to detecting the loading, on the first such microfluidic chip, starting a timer; and, responsive to an impedance change at at least another one of the embedded liquid-presence-sensing electrodes, on the first such microfluidic chip, when the timer has advanced past a first threshold but has not advanced past a second threshold, commencing application of electrokinetic signals to the at least one embedded analytic electrode.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of methods and/or assemblies in accordance with aspects of the invention can be implemented together with computing devices such as a "smart" phone or similar mobile device, and/or in communication with one or more cloud computing nodes in a cloud computing environment. At least some such implementations can make use of suitable software (e.g., for test control and/or analysis of test results) embodied as computer program product including a computer readable storage medium with computer usable program code for performing pertinent method steps based, e.g., on sensor input. A cloud computing node and/or "smart" phone or similar mobile device will include a memory, and at least one processor that is coupled to the memory and operative to perform pertinent method steps. Yet further, in another aspect, one or more embodiments of the invention or elements thereof can be implemented in the form of means for carrying out one or more of the method steps described herein; the means include those disclosed herein. Means for some aspects can include, for example, (i) hardware module(s), (ii) software module(s) stored in a computer readable storage medium (or multiple such media) and implemented on a hardware processor, or (iii) a combination of (i) and (ii); any of (i)-(iii) implement specific techniques.

Techniques of the present invention can provide substantial beneficial technical effects. For example, one or more embodiments solve the problem of obtaining a portable fluorescence reader that includes electronics suitable to generate and excite the electrodes in microchannels, with electrical signals suitable to execute the aforementioned phenomena. One or more embodiments of the present invention provide a portable and compact solution integrating the optical, electrical, mechanical and computational elements required for di electrophoretic manipulation of particles and fluorescent or colorimetric analyte detection. Furthermore, one or more embodiments provide user friendly and user independent operation, which can be controlled remotely, at low cost and low energy consumption.

These and other features and advantages of the present invention will become apparent from the following detailed description of illustrative embodiments thereof, which is to be read in connection with the accompanying drawings.

BRIEF DESCRIPTION OF THE DRAWINGS

FIGS. 16-26 show various views of a third embodiment of a system, in accordance with an aspect of the invention;

DETAILED DESCRIPTION OF PREFERRED EMBODIMENTS

Figure 1:
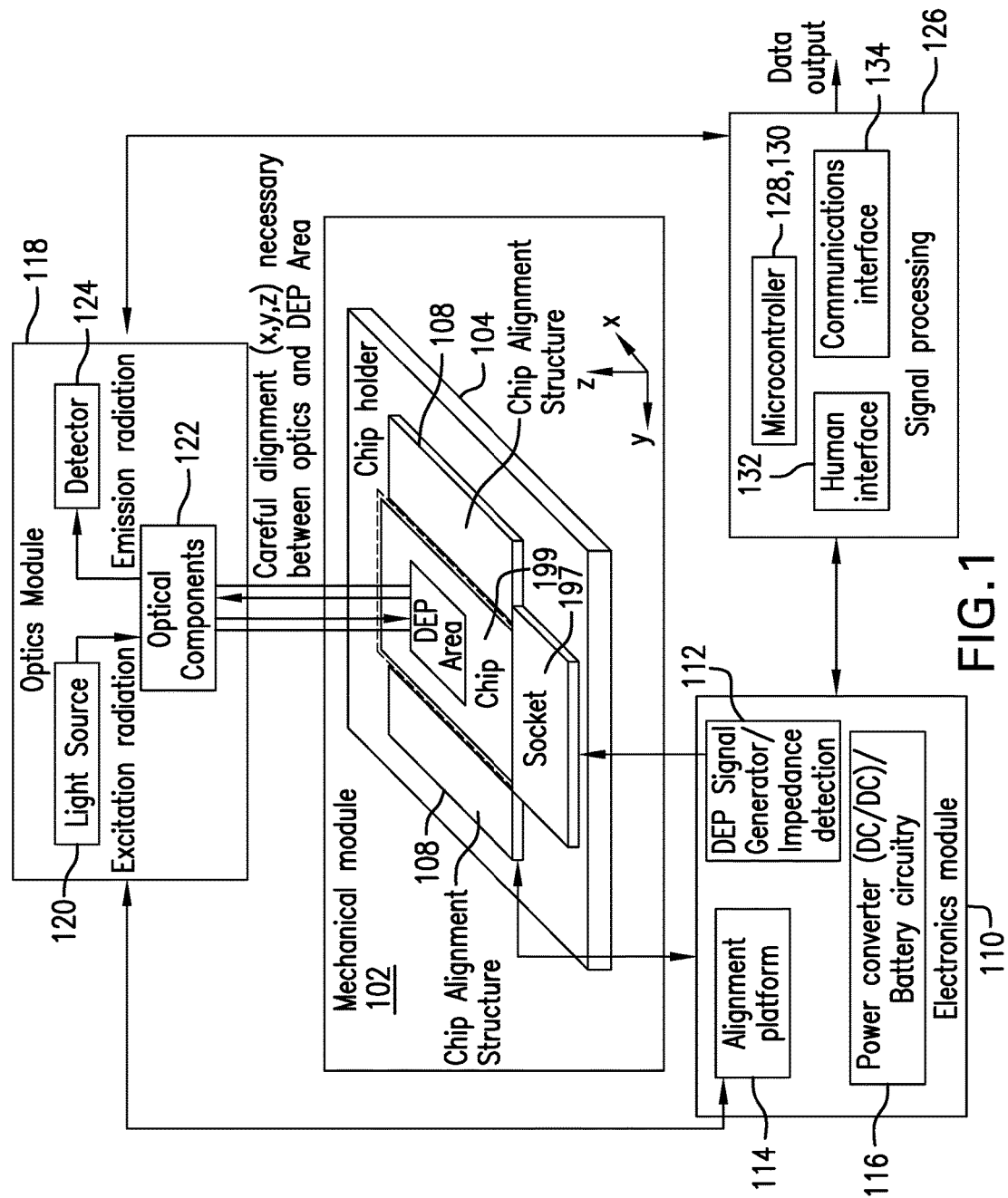
FIGS. 1 and 2 show block diagrams of an exemplary apparatus, in accordance with an aspect of the invention.

One or more embodiments advantageously provide a system that serves to carry out diagnostic operations on microfluidic based chips or devices involving microscopic channels with embedded metallic electrodes. These devices guide the flow of fluids in the microscale, but they also incorporate two key elements:

Embedded metallic electrodes creating an electric field in the microchannel capable of manipulating the fluid and suspended microparticles (in particular, metallic electrodes deposited on areas of the microchannel walls capable of creating an electric field distribution inside the fluid flowing along the microchannel with useful effects over the fluid and suspended microparticles that manifest themselves only in the microscopic scale);

A diagnostic based on the detection of fluorescent emission from the target molecules (typically, from fluorescence labels attached to the target molecules).

Fluorescent detection often requires expensive and bulky fluorescent microscopes, while additional electrical equipment is needed to power the electrodes, making the entire setup expensive, cumbersome and hardly portable, relying on laboratory infrastructure to be able to operate properly.

One or more embodiments provide a portable and significantly more affordable apparatus, including a microfluidic chip carrier and peripherals with electrical, optical, and wireless addressing capabilities, including four main modules:

A mechanical module to facilitate chip manipulation
  An electronics module to power and control the electrodes operation
  An optical detection module
  A signal processing and communication module.

In one or more embodiments, the modules are operated according to the following sequence:

Chip loading, alignment and sample input
  Electric signal control to drive analysis
  Optical detection
  Result processing and communications of final diagnostic.

With regard to microfluidic chips in the context of portable sensing, microfluidic chips can be powerful devices for performing (bio)analysis: many types of reagents can be integrated to microfluidic devices and the high precision with which liquids and samples can be moved throughout microfluidic devices, combined with very small liquid volumes, enable fast, precise and sensitive assays to be performed. The small form factor of microfluidic chips also make them well suited for portable sensing applications (e.g. point-of-care testing, environmental monitoring, diagnostics in poor settings areas, etc.). However, depending on the sensing mechanism, microfluidics chip layout, and assay principles, peripherals may be needed. Interfacing peripherals with chips is not a trivial problem because:

1. Chips and peripherals should all together support portability.
2. The chips should be easily and reliably interfaced/removed with/from peripherals by non-technical experts.
3. Operating the chips and peripherals with samples should be safe, with a suitable operation procedure to avoid cross-contamination between different samples.
4. The chips and peripherals should allow using capillary-driven flow (this requires vents and a loading pad for placing a sample, and provides relief from using bulky, expensive active pumping techniques).
5. It is also advantageous to have electrical connections to the chip for e.g. monitoring and flow control, detecting electroactive species, or concentrating particles via dielectrophoresis.
6. It is also advantageous to have a well-defined optical path to some areas of the chip for optical monitoring and reading optical signals, such as fluorescence or colorimetric signals.
7. It is also advantageous to have the chip connected to a mobile computing device to provide access to the Internet and/or to use the mobile computing device for local data processing and aggregation.
8. Finally, chips should be small to minimize manufacturing costs; in particular, when Si wafers and microtechnology are used for producing chips. In addition, small chips would require small sample volumes, which provide ease in analysis and faster chemical/immunoassay reactions, necessary to obtain quick results.

We have found that it is appropriate to take steps to minimize corrosion and contamination. The alternating current (AC) fields needed for dielectrophoresis put strong limitations on the metals that can be used. Pd, Pt, or Au are typically used for these reasons; however, they are very expensive and need to be patterned as thin layers. This creates significant wear/contact challenges. We have found that it is desirable to avoid relying on sliding sockets only, where practicable. Chips are typically small (1 to 2 $cm^2$) to minimize fabrication cost. Due care should be taken when using small chips to manage any safety issues with overflow of sample (e.g. blood for infectious diseases diagnostics). The liquid loading pad, detection area and electrical contacts are typically located on the same side of the chip. Additionally, we have found that the loading pad, detection area, and electrical contacts should preferably not be placed too close to each other, to minimize risk of sample overflow and electrical shorts or surface contamination. Given the teachings herein, including these guidelines, the skilled artisan will be able to appropriately locate these features for particular applications of embodiments of the invention.

Capillary filling needs vents for displacing air during filling of the chip. Liquids should not leak out of the chip or through vents for safety and contamination reasons. Electrical contacts should not occupy too much space on the chip, while yet being present in sufficient numbers for proper chip operation. We had poor experience with directly inserting chips to a socket with spring loaded contacts because the translational (x, y, z) positioning and/or alignment of the chip with respect to an optical reader was not reproducible. In particular, chips tended to be tilted and partially out of focus, perhaps because the spring loaded electrical contacts were pressing the laterally inserted chips differently each time.

In some applications, microfluidic chips present certain areas within the microchannel containing electrodes, which can be long and parallel, short, in the form or arrays or other shapes, such that they can be used for trapping various populations of beads. Furthermore in this regard, note that some versions of the microfluidics chips include bead sorting capabilities. For example, such chips are capable of sorting beads with different diameter or sorting beads that are made of different materials. Positioning the optical system on a specific area required using a large and expensive fluorescence microscope stage. Reading optical signals on the chips may require various magnifications or light wavelengths. Therefore, the chip should not have physical structures (e.g. loading pad) that might collide with optical lenses or components. A 1 mm up to 1 cm optical working distance is desired.

Stray light might be detected and lead to false positives. Electrical cross-talk (interference) for high frequency signals (e.g. DEP) should be avoided.

Heretofore, problems have arisen in the electrical connection of microfluidic devices and a fluorescence reader. Fluorescence microscopes are expensive and bulky. They provide proper excitation light at the absorption wavelength and high quality filters for separating the much weaker fluorescent radiation from the excitation light. They can be equipped with very high sensitivity and low noise cameras with Peltier cooling, which obtains super high resolution fluorescence images and videos. They are also very expensive equipment not suitable for low cost PoC applications (>$50 k). They are used in connection with an electronic laboratory bench signal generator, and require a laboratory infrastructure.

Lower cost and portable optical measurement devices or readers with a miniaturized fluorescence optical detection system (LED illumination, focusing lens, dichroic mirror and photodetector) have also been used heretofore, but these solutions are appropriate only for cellulose or paper strips (i.e. lateral low assays (qualitative)). Although cheaper than a Fluorescence Microscope, these systems still cost several thousands of dollars (typically ~$8K-10K). Current systems do not include the electronics necessary to power the electrodes embedded in the microchannels.

Microfluidic chips for fluorescence-based assays not only need a fluorescence optical setup but can also require an actuation and/or excitation source for the electrodes (e.g. for DEP). Using contact pads on a microfluidic device, with an electrical socket and peripheral wave signal generator is cumbersome (cables, microscopes, oscilloscopes and various peripherals are needed). As alluded to above, stray light, vibrations and motions of the microfluidic device can negatively affect fluorescence signal measurements.

One or more embodiments consider the following design constraints and requirements, due to the detection methodology used, and the small dimensions and materials used on the microfluidics chip. Other embodiments could take a different approach. Fluorescence analysis (excitation and fluorescence light) is executed from the top of the chip, because it is made of silicon (which is opaque). Only the chip cover is transparent and the sample is therefore deposited from the top. The platform aligns carefully to the laser spot with respect to the DEP area (on the x, y and z directions), so that the fluorescence signal is correctly obtained and a correct analysis is executed. For optimal fluorescence signal (i.e.: maximize DEP area filled with microbeads), DEP signal amplitude and time multiplexing (turning on/off DEP signal) is also an appropriate method. Time multiplexing depends on the bead size and flow speed (which is determined by the microfluidics chip characteristics, such as height and width of the microchannels). One or more DEP signal generators, which can be individually adjusted in amplitude and frequency, are used in different electrode pairs, in which the function can be sorting (e.g.: isolate a certain bead with a specific diameter or with certain composition) or trapping to detect the fluorescence from the beads. Again, electric contacts should be as far as possible from the loading pad, to avoid biohazard contamination of the mechanical interface between the microfluidics chip and the socket and/or mechanical chip handler. Complete darkness is required, due to interference that room illumination and/or sunlight causes in fluorescence detection. Hence, a black container is used in one or more embodiments to eliminate external light and provide separation between optical and electrical modules to avoid interference.

For correct fluorescence analysis, the microfluidics chip should be fixed in the proper position; one or more embodiments employ a chip alignment structure made of a suitable material (plastic is one non-limiting example), with suitable format, to keep the chip in the same position, as compared with the electrode socket. The fluorescence reader should be convenient for use by the end user, so that there are essentially three steps to execute an analysis: insert the microfluidics chip in the socket; pipette the sample; and start fluorescence analysis.

Figure 2:
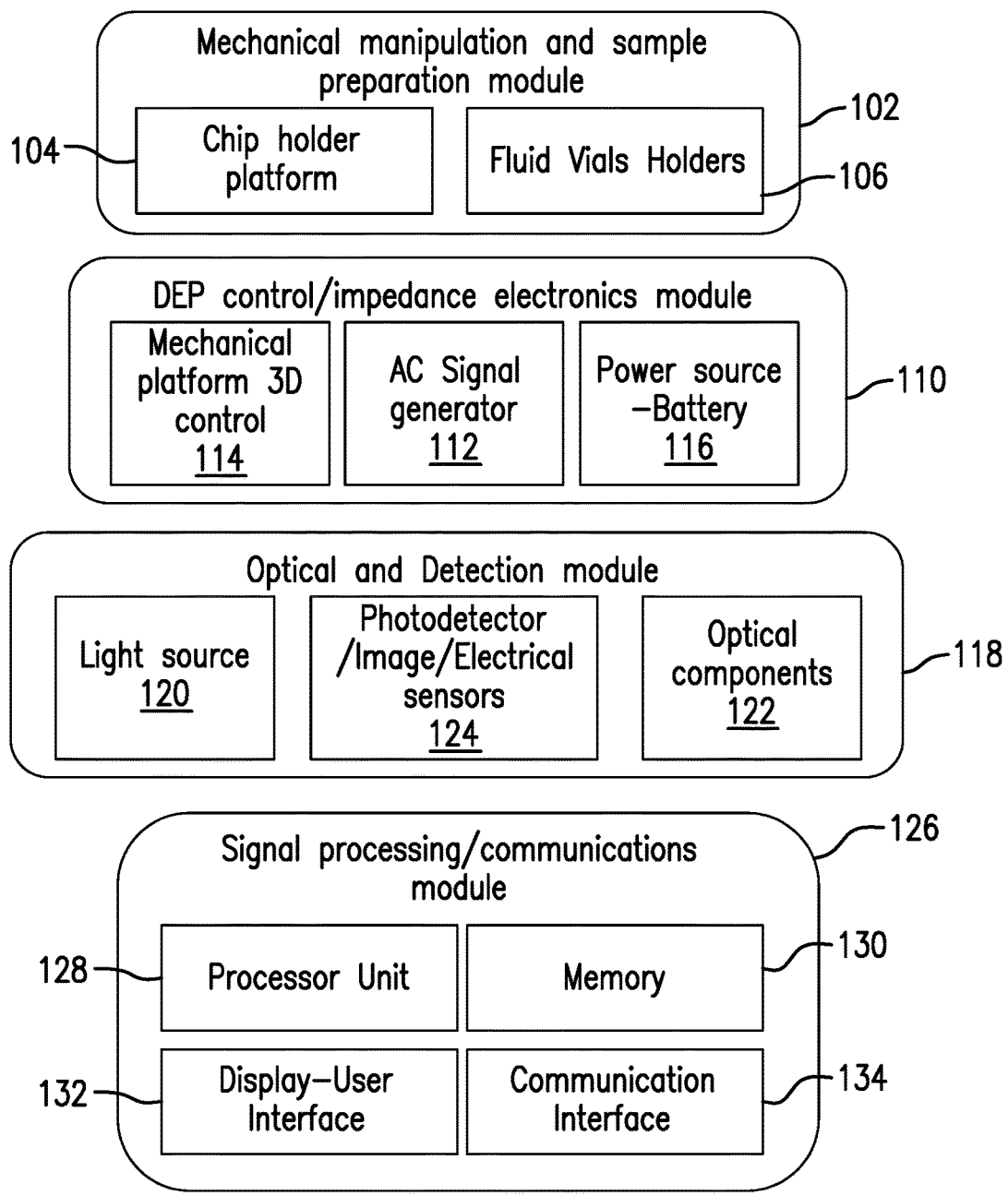

FIGS. 1 and 2 show block diagrams of an exemplary apparatus, in accordance with an aspect of the invention. In one or more embodiments, a portable apparatus includes mechanical and electronic components necessary to power electrodes that are integrated to a microfluidic device, a fluorescence detection module, and a signal processing and communications module. In a non-limiting exemplary embodiment, the mechanical module 102 includes mechanical elements to manipulate the chip as well as other sample preparation and/or post-processing elements such as for rinsing or mixing with other fluids, and the like. For example, mechanical module 102 can include chip holder platform 104, fluid vials and holders 106, socket 197 and alignment structures 108.

In the non-limiting exemplary embodiment, electro-kinetic (DEP) control electronics module 110 controls the electrode excitation operation and includes AC signal generator 112, electronics 114 for the control of the mechanical parts in charge of alignment between the microfluidics chip and optical components 122, and a power source and/or battery control circuit such as 116.

Furthermore, in the non-limiting exemplary embodiment, in detection or optical module 118, the interface to the biological signal can be optical (fluorescent or colorimetric) or can be based on other physical properties (impedance, magnetic, etc.). Module 118 also includes light source 120 and optical elements (lens, filters) 122, and a photodetector, image sensor, and/or camera 124, which can be modified, depending on the detection method.

Finally, in the non-limiting exemplary embodiment, signal processing and communications module 126 includes a processor unit 128, memory 130, display and/or other user interface 132, and communications interface 134 (which can be wired and/or wireless). In some instances, the processor and memory are provided as part of a microcontroller, as seen in FIG. 1.

Figure 3:
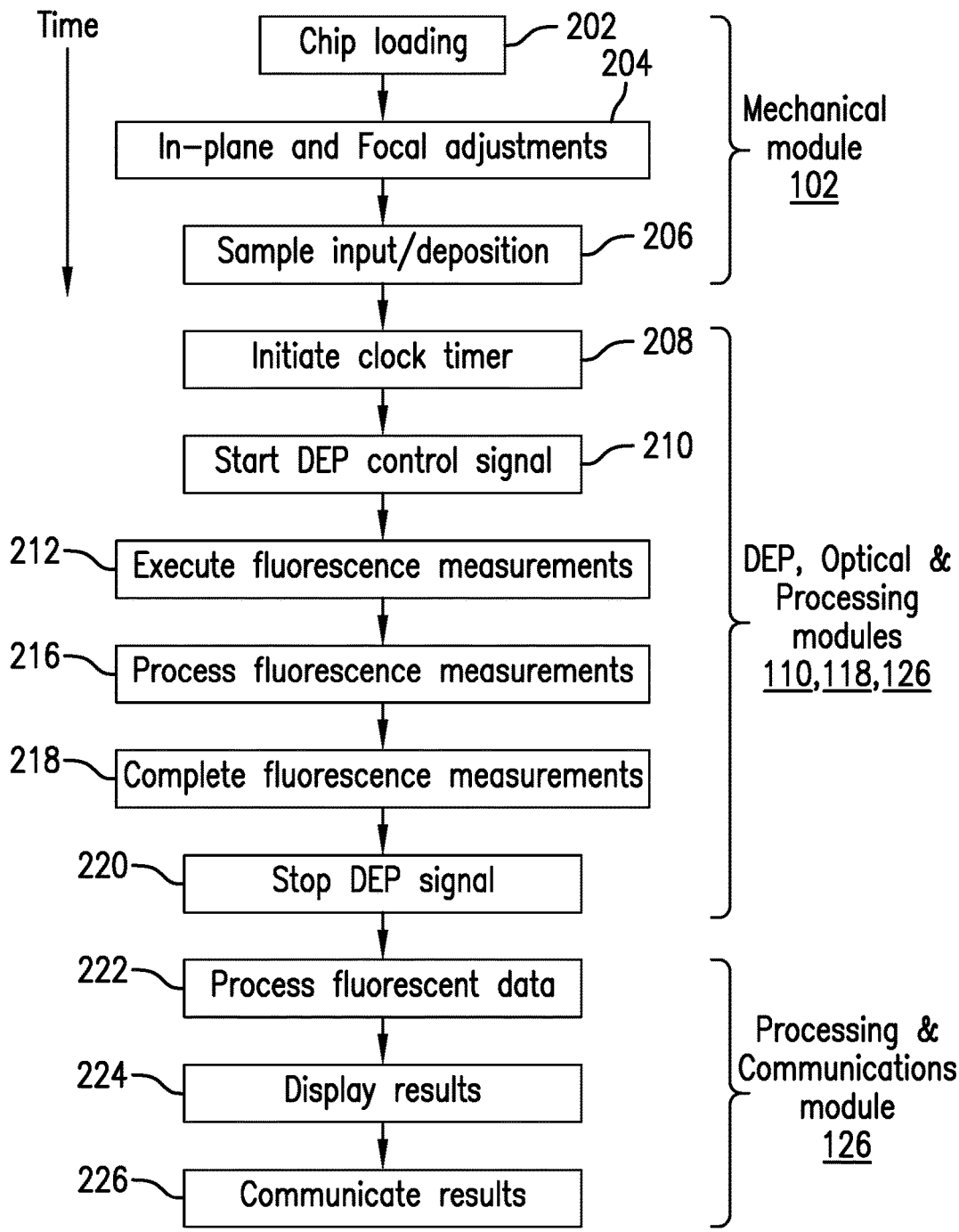
FIG. 3 shows a flow chart of an exemplary method, in accordance with an aspect of the invention.

Continuing to refer to FIGS. 1 and 2, and referring now also to the flow chart of FIG. 3, operation of the system once the chip is inserted (e.g., chip 199 is inserted into socket 197) is made autonomous by following several pre-determined steps. The user, through a user interface 132, can adjust the reader device to properly execute the desired analysis. The steps depicted in FIG. 3, in the non-limiting example shown, are depicted in chronological order starting with the first and proceeding to the last. Other embodiments can use a different order of the referred steps, and/or add or omit some steps, if appropriate. Step 202, carried out by mechanical module 102, includes chip loading. Optionally, in step 204, mechanical module 102 undertakes chip platform adjustments, which can follow a fixed sequence, or if visual of the chip is available, can include real-time adjustments to optimize the fluorescence signal. Step 204 can also include focal adjustment and/or in-plane alignment. Step 206, carried out with the aid of mechanical module 102, includes sample input and/or deposition, which is executed by the user.

In optional step 208, an experiment clock can be initiated by signal processing module 126 in order to follow a pre-determined and pre-timed sequence that allows the sample to fill up the microfluidics channel until it reaches the DEP signal and fluorescent measurement region. In step 210, signal processing module 126 starts the DEP signal generator 112. In step 212, optics module 118 executes fluorescence measurement. In step 216, the fluorescence measurement is processed by signal processing module 126. In step 218, optics module 118 finishes the fluorescence measurements. In step 220, the signal processing module 126 stops the AC signal generator 112.

In step 222, signal processing module 126 processes the fluorescent data; in step 224, module 126 displays the results via human interface 132; and in step 226, module 126 provides the results to external devices (e.g.: cloud server 12 discussed below) via communications interface 134. Not every embodiment will necessarily include both step 224 and 226.

While an experimental clock can be initiated in order to follow a pre-determined and pre-timed sequence of DEP signal and fluorescent measurement, alternatively, the signal sequence control can use feedback from the experiment (optical, electrical, magnetic or otherwise). Similarly, the detection signal can be measured at a fixed window of time and/or number of measurements after the experiment has started, as defined based on prior experience, or the signal can be measured continuously until an indication that saturation has been reached. Finally, results can be displayed and/or transferred wired and/or wirelessly to a database server or other suitable destination, for further processing.

Figure 4:
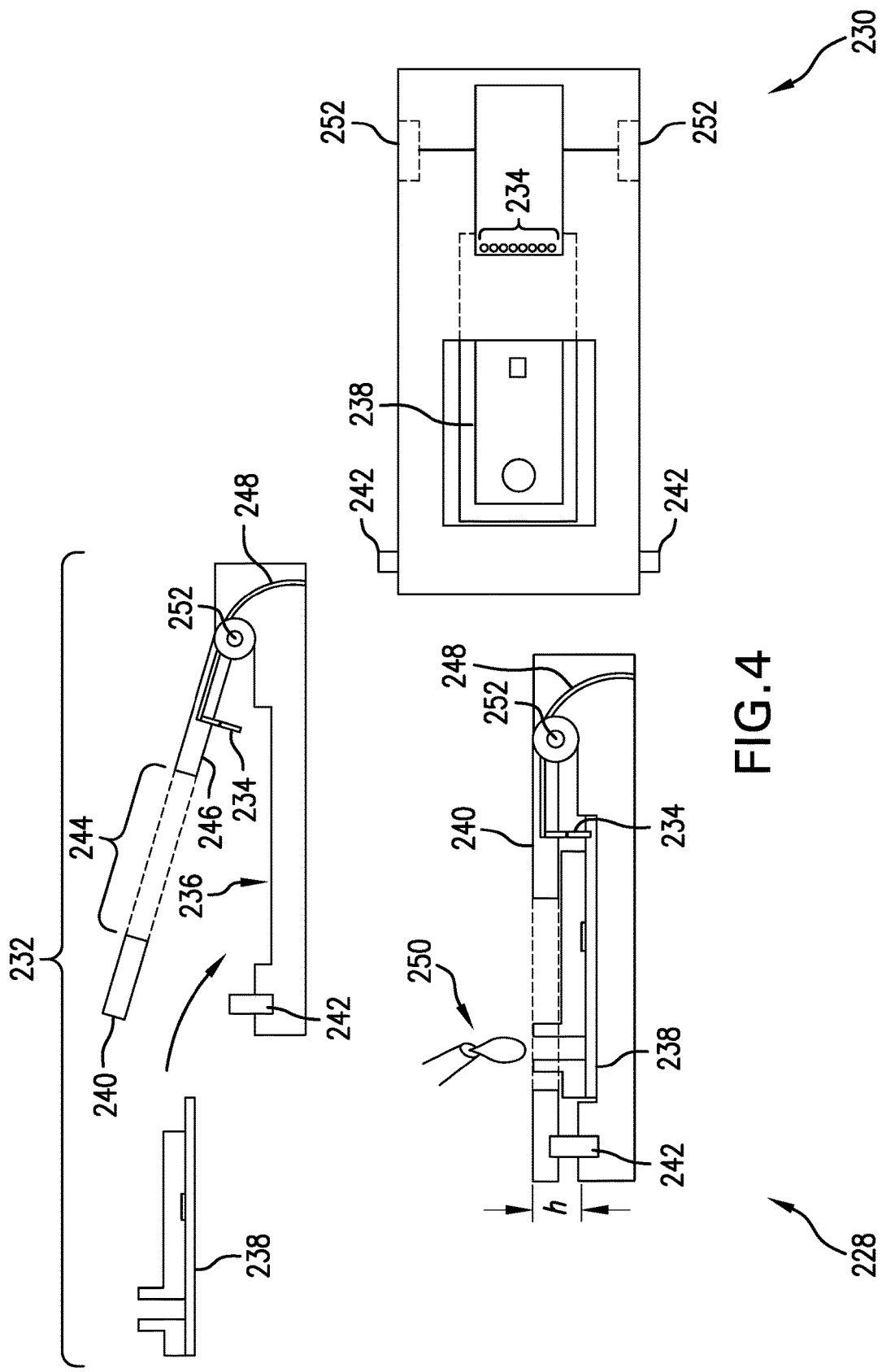
FIG. 4 shows several views of an exemplary chip holder with folding frame design for microfluidic chips, in accordance with an aspect of the invention.

FIG. 4 shows several views of an exemplary folding frame for microfluidic chips, in accordance with an aspect of the invention (e.g., for use in the mechanical module 102). In particular, view 228 is a side view, view 230 is a top view, and view 232 depicts chip insertion. The exemplary folding frame provides mechanical, electrical, optical, and, on some embodiments, wireless addressing capabilities with various peripherals. Note out-of-plane spring-loaded electrical contacts 234 (e.g. Pogo-pin), which provides a greater number of contacts in a small chip area; cavity 236 to place and align the chip 238; and spring-loaded cover 240 with lock and unlock mechanism 242. Cover 240 presses the chip from the top for mechanical fixity, electrical contact purposes, and also to maintain chip flatness for better focusing. In some cases, the bottom side 246 of the cover 240 can have a hydrophobic cushion layer for compliancy and to prevent liquid leakage to the contacts 234. Also provided is an opening 244 in the cover 240 to allow liquid loading (seen at 250) and optical detection. Optionally, a mechanism can be added to "lever up" the chip for easier removal when measurement is done. A flexible cable 248 connects with the contacts 234. Note also hinges 252.

In one or more embodiments, the height h should be carefully controlled for optical read-out at potentially high magnification.

One or more embodiments are advantageously low cost, easy to operate, and can be interfaced with many peripherals.

Figure 5:
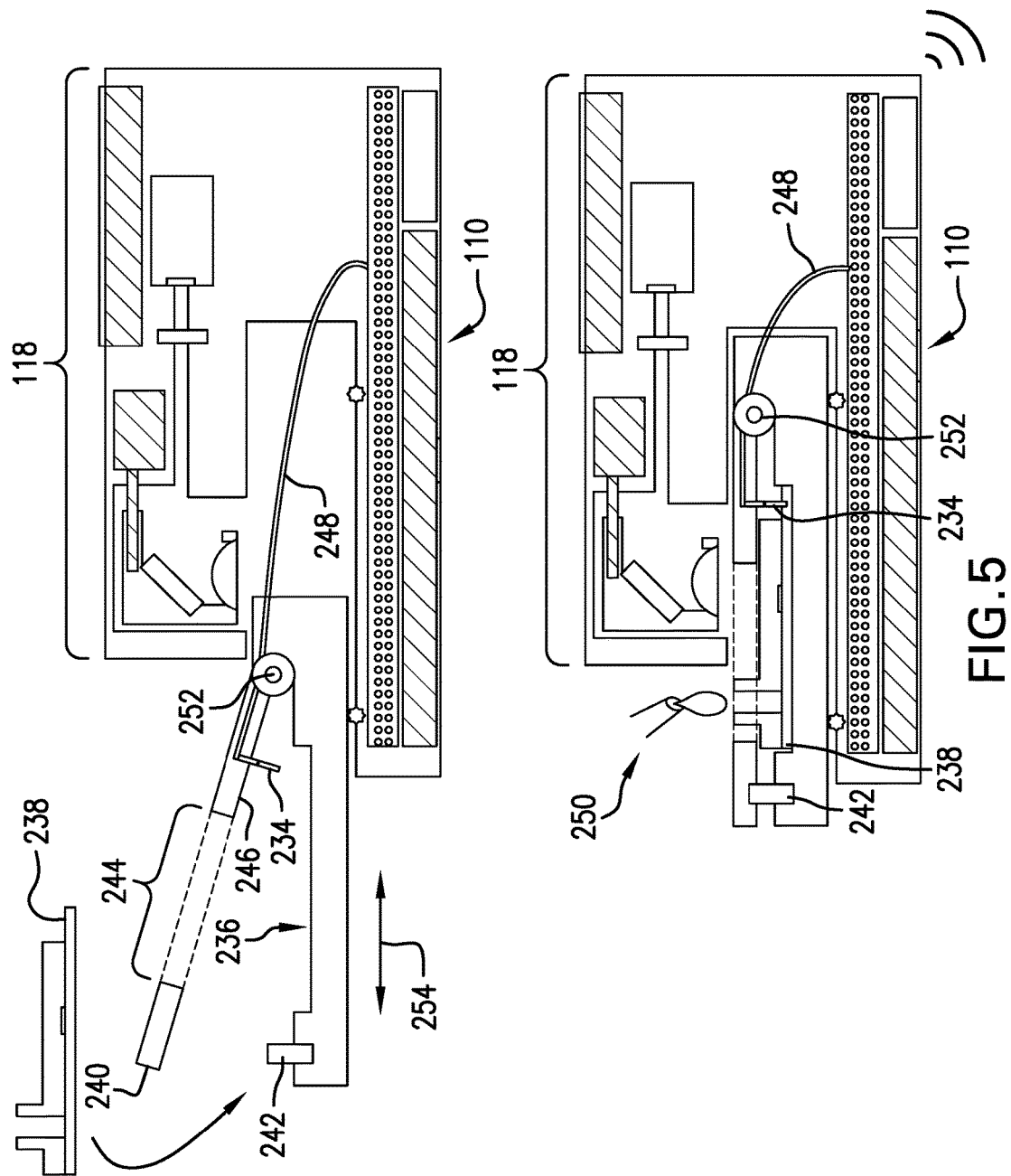
FIG. 5 shows a first exemplary detailed form of an exemplary chip holder with folding frame design for microfluidic chips, wherein the frame is combined with an optical reader and electronic module, in accordance with an aspect of the invention.

FIG. 5 shows a first exemplary detailed form of an exemplary folding frame for microfluidic chips, wherein the folding frame is combined with an optical reader module 118 and electronic module 110 using a tray mechanism, in accordance with an aspect of the invention, obtaining a fully functional detection unit. Advantages include ease of chip handling, compactness, portability, and stand-alone capability. Furthermore, the tray can be moved for scanning, as seen at 254, which simplifies the optics. Yet further, the frame can be replaced for different chip dimensions, layout and/or versions, which results in a more flexible design. In one or more embodiments of this type, the chip is electrically connected and/or powered early on (for example, even before the sample is loaded), such that the flow can be monitored right from the beginning of the process. The electronics module 110 detects if a chip is present and also that the electrical contacts are functioning properly (e.g., via capacitance measurements).

Figure 6:
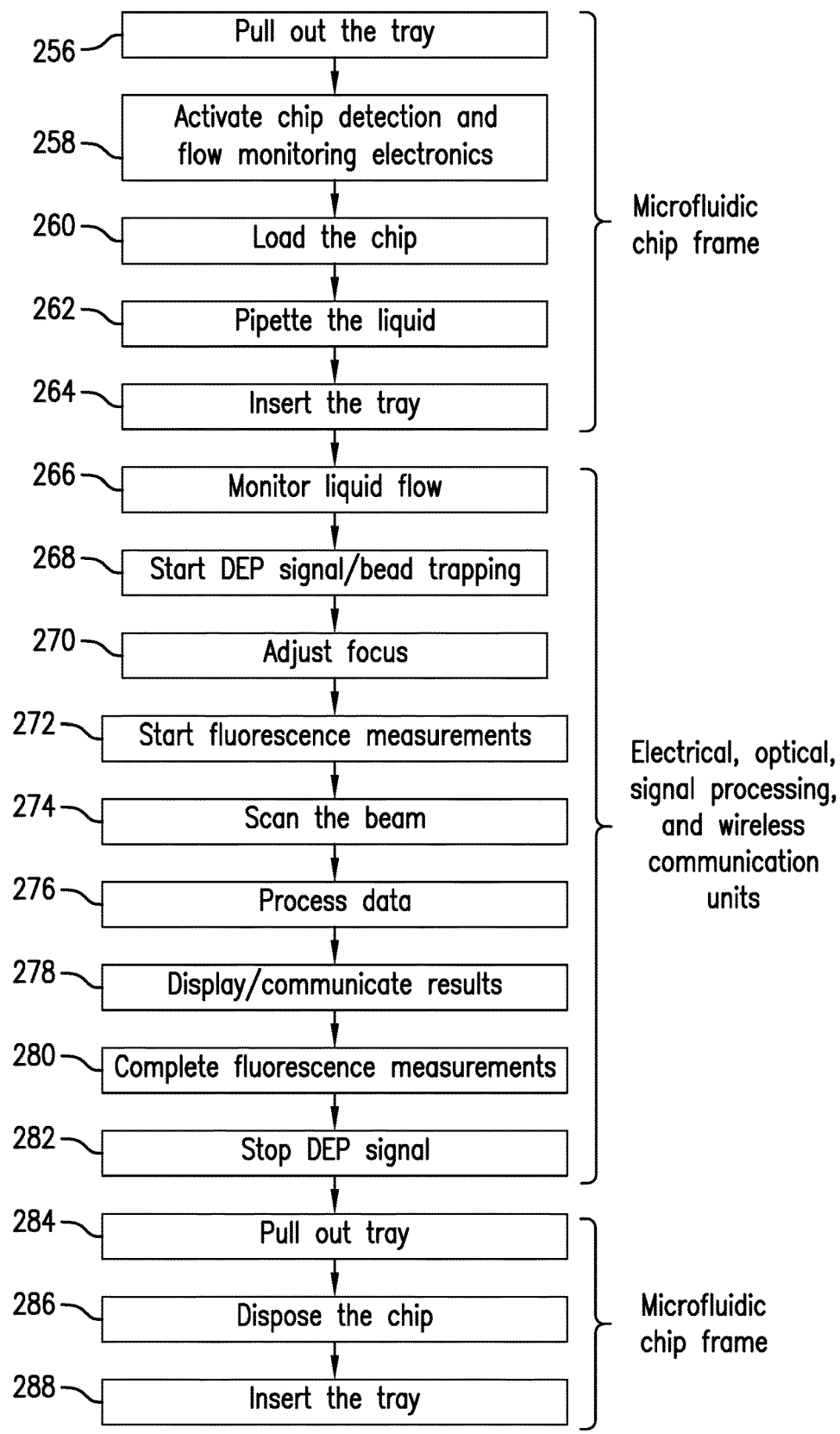
FIG. 6 shows a flow chart of an exemplary detailed method useful with respect to the frame of FIG. 5, in accordance with an aspect of the invention.

FIG. 6 shows a flow chart of an exemplary detailed method useful with respect to the frame of FIG. 5, in accordance with an aspect of the invention. Steps 256, 258, 260, 262, and 264 pertain to the microfluidic chip frame per se. In step 256, pull out the tray, to provide access to chip cavity 236. In step 258, activate the chip detection and flow monitoring electronics. In step 260, load the chip into cavity 236. In step 262, pipette the liquid into microfluidics chip loading pad. In step 264, insert the frame into the tray.

Steps 266, 268, 270, 272, 274, 276, 278, 280, and 282 pertain to the electrical, optical, signal processing, and wireless communication units. In step 266, monitor the liquid flow, to track when the liquid sample meniscus arrives and fills up the DEP area. In step 268, start the DEP signal and bead trapping. In step 270, adjust focus. In step 272, start the fluorescence measurements. In step 274, scan the microfluidics chip with the optics. In step 276, process the data. In step 278, display and/or otherwise communicate the results. In step 280, complete the fluorescence measurements. In step 282, stop the DEP signal.

Steps 284, 286, and 288 pertain to the microfluidic chip frame per se. In step 284, pull out the tray to have access to the used chip. In step 286, dispose of the chip, in compliance with any applicable rules, regulations, or procedures pertaining to biological/medical samples or the like. In step 288, insert the frame into the tray.

Figure 7:
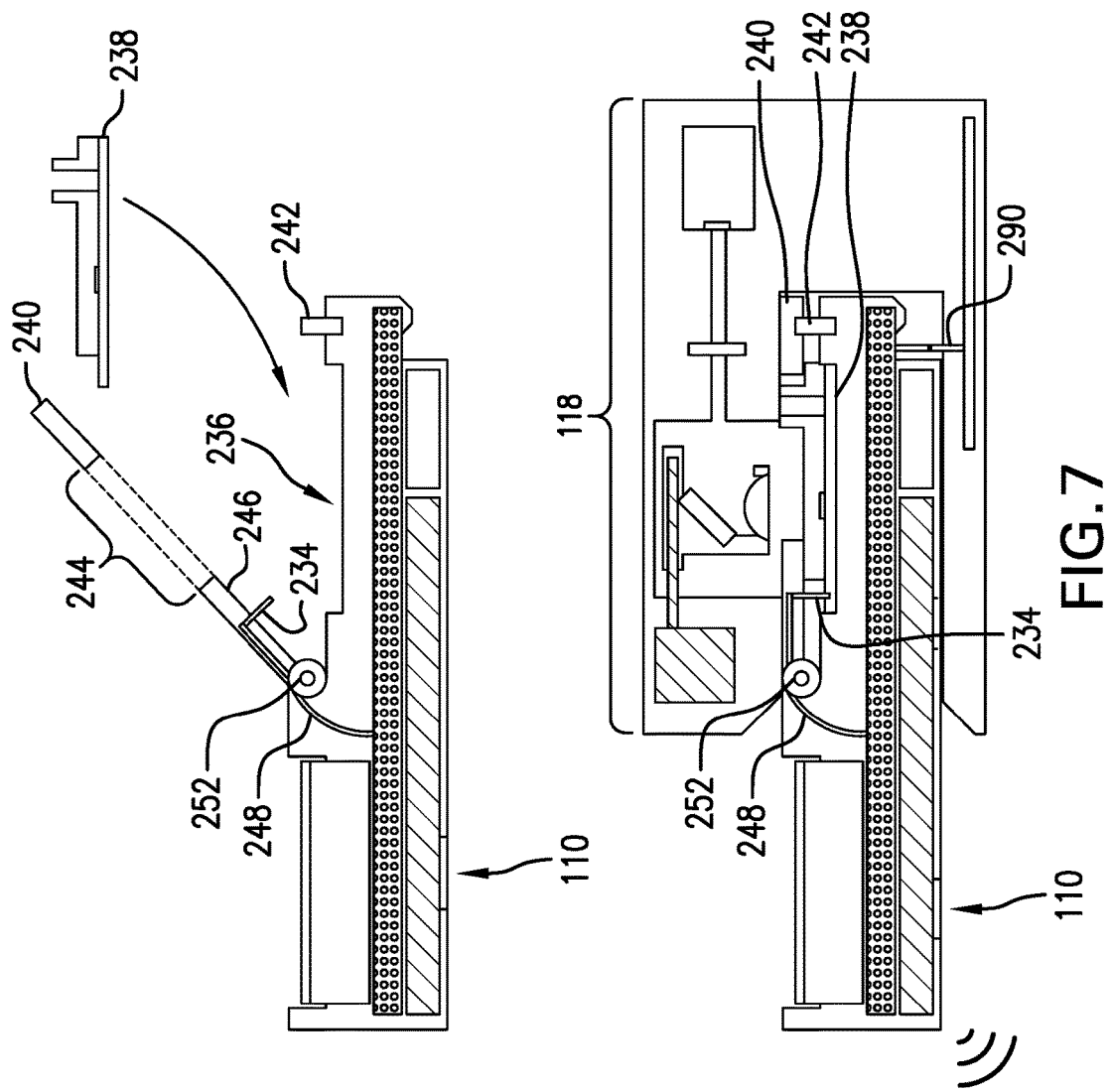
FIG. 7 shows a second exemplary detailed form of an exemplary chip holder with folding frame design for microfluidic chips, wherein the optical reader and electronic module are two independent units, in accordance with an aspect of the invention.

FIG. 7 shows a second exemplary detailed form of an exemplary folding frame for microfluidic chips, wherein the optical reader and electronic module are two independent units, in accordance with an aspect of the invention. In particular, the optical unit 118 is separate from the frame, as in FIG. 5, but the frame includes electronics module 110. In this way, tests can be run in parallel with only one optical reader needed to measure final results. The tighter integration with electrical connections provides less parasitics, improving measurement precision, and the approach is compatible with "electrical" detection techniques (e.g. impedimetric and/or electrochemical assays). Additional contacts 290 are provided for electrical communication between the optical reader and electronic module.

Figure 8:
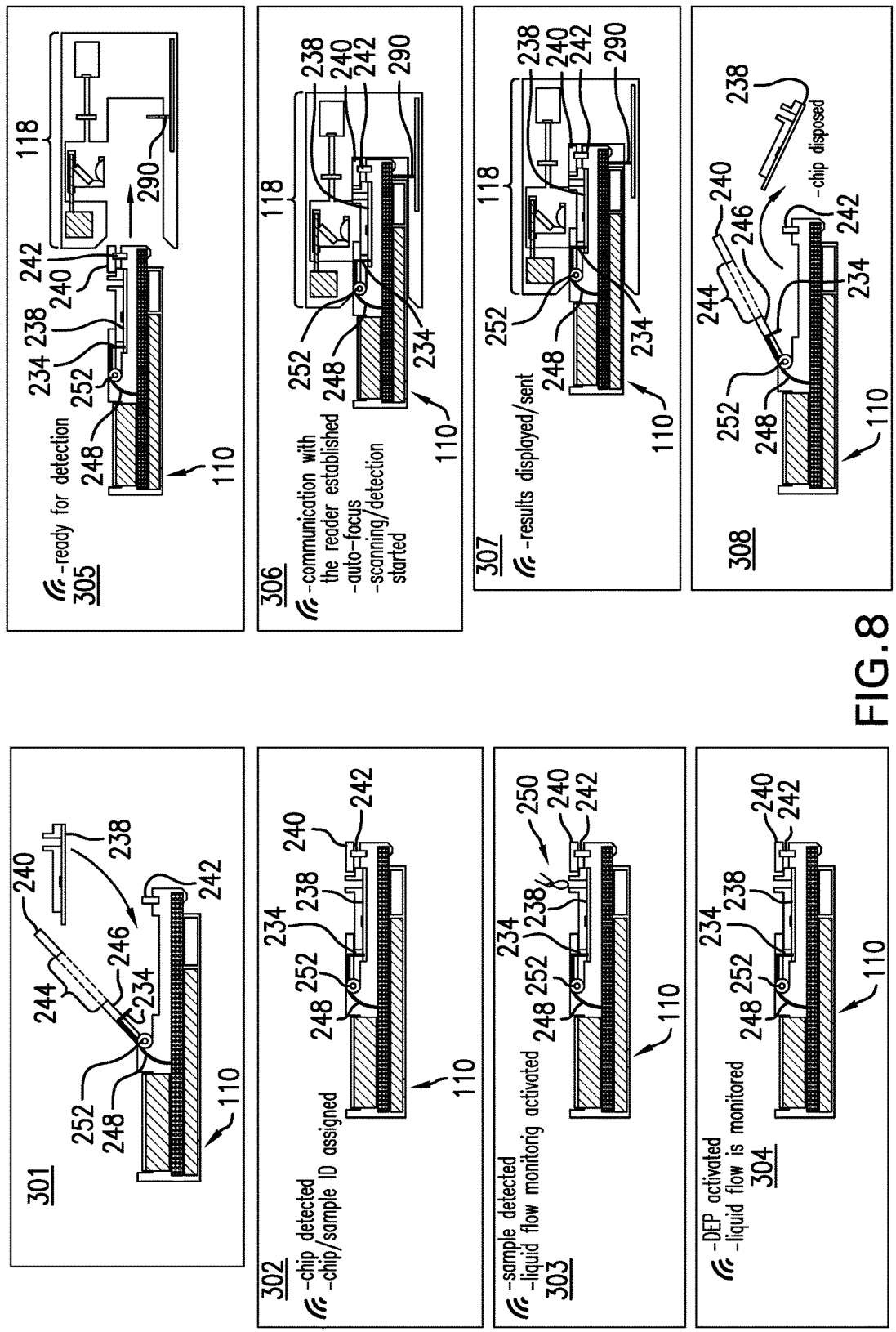
FIG. 8 shows an exemplary series of workflow steps and protocol, useful in connection with the frame of FIG. 7, in accordance with an aspect of the invention.

FIG. 8 shows an exemplary series of workflow steps and protocol, useful in connection with the frame of FIG. 7, in accordance with an aspect of the invention. In a first step 301, insert the chip 238 into the frame. In a second step 302, the chip is detected and a chip and/or sample ID (identifier) is/are assigned. In a third step 303, the sample is detected and liquid flow monitoring is activated. In a fourth step 304, the DEP is activated when the liquid arrives at the DEP region and the liquid flow is monitored. In a fifth step 305, the combined frame and electronics module are ready to be inserted into the optics module 118 for detection. In a sixth step 306, communication with the reader is established, auto focus is carried out, and scanning and detection are commenced. In a seventh step 307, the results are displayed and/or sent elsewhere. In an eight step 308, the chip 238 is disposed of.

Figure 9:
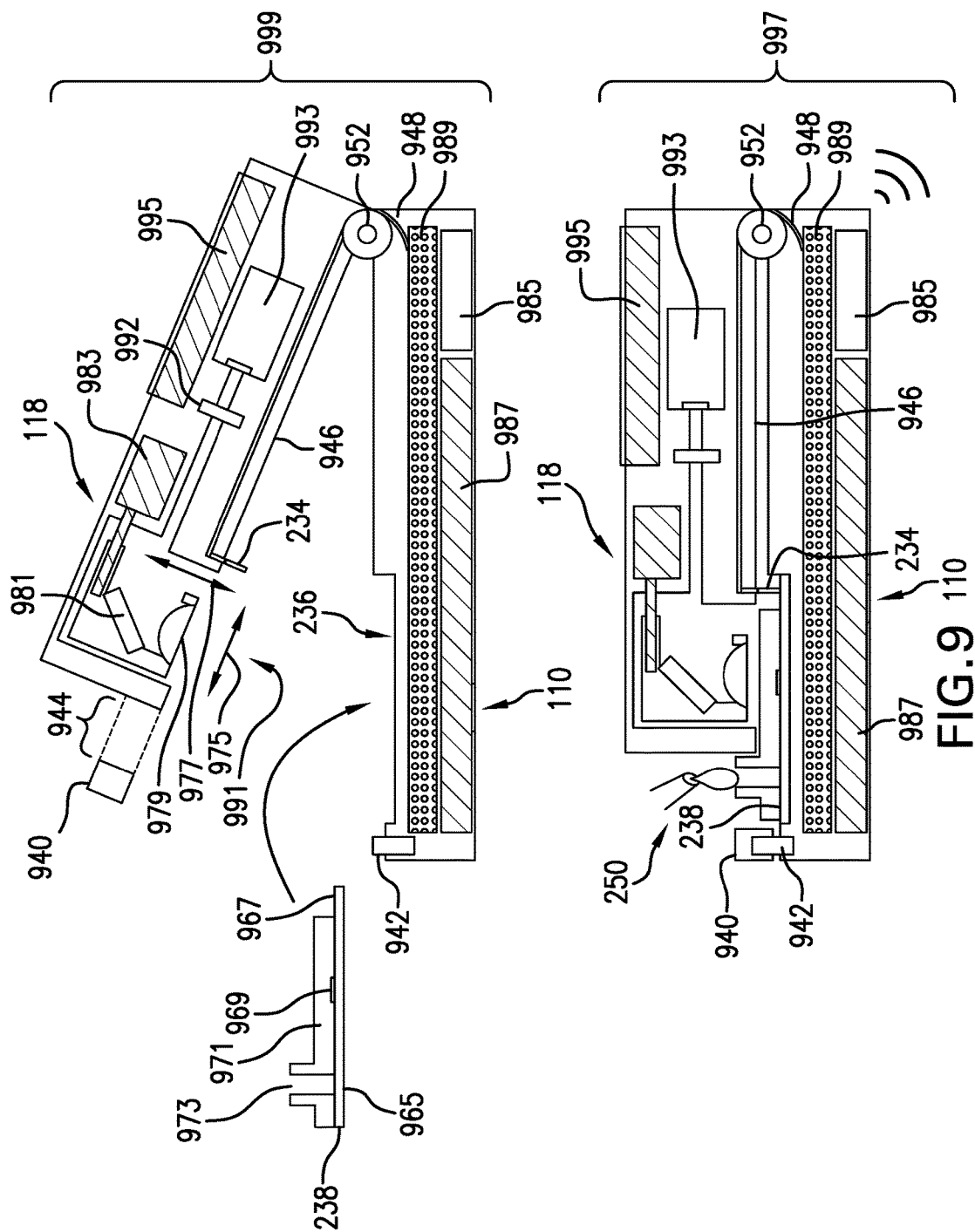
FIG. 9 shows a third exemplary detailed form of an exemplary chip holder with folding frame design for microfluidic chips, wherein the optical reader and electronic module are integrated to the folding frame, in accordance with an aspect of the invention.

FIG. 9 shows a third exemplary detailed form of an exemplary folding frame for microfluidic chips, wherein the optical reader and electronic module are both integrated into the frame, in accordance with an aspect of the invention. View 999 is a side view with the frame open to receive the chip 238, while view 997 is a side view with the chip inserted. Elements essentially the same as those discussed above have received the same reference character; while, as will be appreciated by the skilled artisan, elements in this alternative embodiment which are generally analogous to those discussed above have received the same reference character incremented by seven hundred. The spring-loaded cover 940 has a lock and unlock mechanism 942. In some cases, the bottom side 946, the cover 940, and the cavity 236 can have a hydrophobic cushion layer for compliancy and to prevent liquid leakage to the contacts 234. Also provided is an opening 944 in the cover 940 to allow sample loading (seen at 250). A flexible cable 948 connects with the contacts 234. The top and bottom sides are connected by hinges 952.

The hinged cover 940 includes light source and detector 993, a display 995 for visual feedback, filters 992, and optics with beam scanning and focusing 991, while the bottom portion of the frame (not separately numbered) includes the electronics module 110, wireless communication unit, and battery. In particular, electronics module 110 can include main board 989, battery 987, and wireless unit 985. Furthermore, the optical unit 118 can include, for example, a mechanical unit 983 (e.g., including a stepper motor to impart linear motion), a mirror 981 and lens 979, and a microcontroller with USB interface. Focusing is as shown at 977 (up and down as compared to sample when assembly is closed) while beam scanning is as shown at 975 (back and forth as compared to sample when assembly is closed, as well as into and out of the plane of the paper, so as to scan a planar region). In a non-limiting example, the beam scanning range of motion can be 1-2 cm. Furthermore, in a non-limiting example, the optical unit can have dimensions of 50 mm wide by 80 mm long by 50 mm high, an optical working distance of 1-10 mm, and a detection area/resolution of 1 $\mu m^2$ (single bead detection) and 0.01-10 $mm^2$ (integrated area).

Exemplary advantages of the embodiment of FIG. 9 include compactness, portability, stand-alone capability, and ease of use. Furthermore, overspill of the sample is easier to clean, inasmuch as the loading pad is left out of the closing part of the frame.

In a non-limiting example, the microfluidic chip can have dimensions of about 10 mm width, 30 mm length, and 2 mm thickness, and can handle a liquid volume of from 1-10 μL. Furthermore, the mobile electrical unit can have, for example, dimensions of 30 mm width, 80 mm length, and 20 mm height. The DEP signal can, for example, range from 5-25 Vpp at a frequency of 100 kHz-3 MHz. Flow monitoring can be carried out at, for example, 1-5V at frequencies from DC up to 100 kHz.

In a non-limiting example, the microfluidic chip 238 includes electrical contacts at 967, a detection area at 969, a plastic housing 971, a loading pad 973, and a chip substrate 965 with microfluidic channels and microelectrodes.

First Exemplary Embodiment

Figure 10:
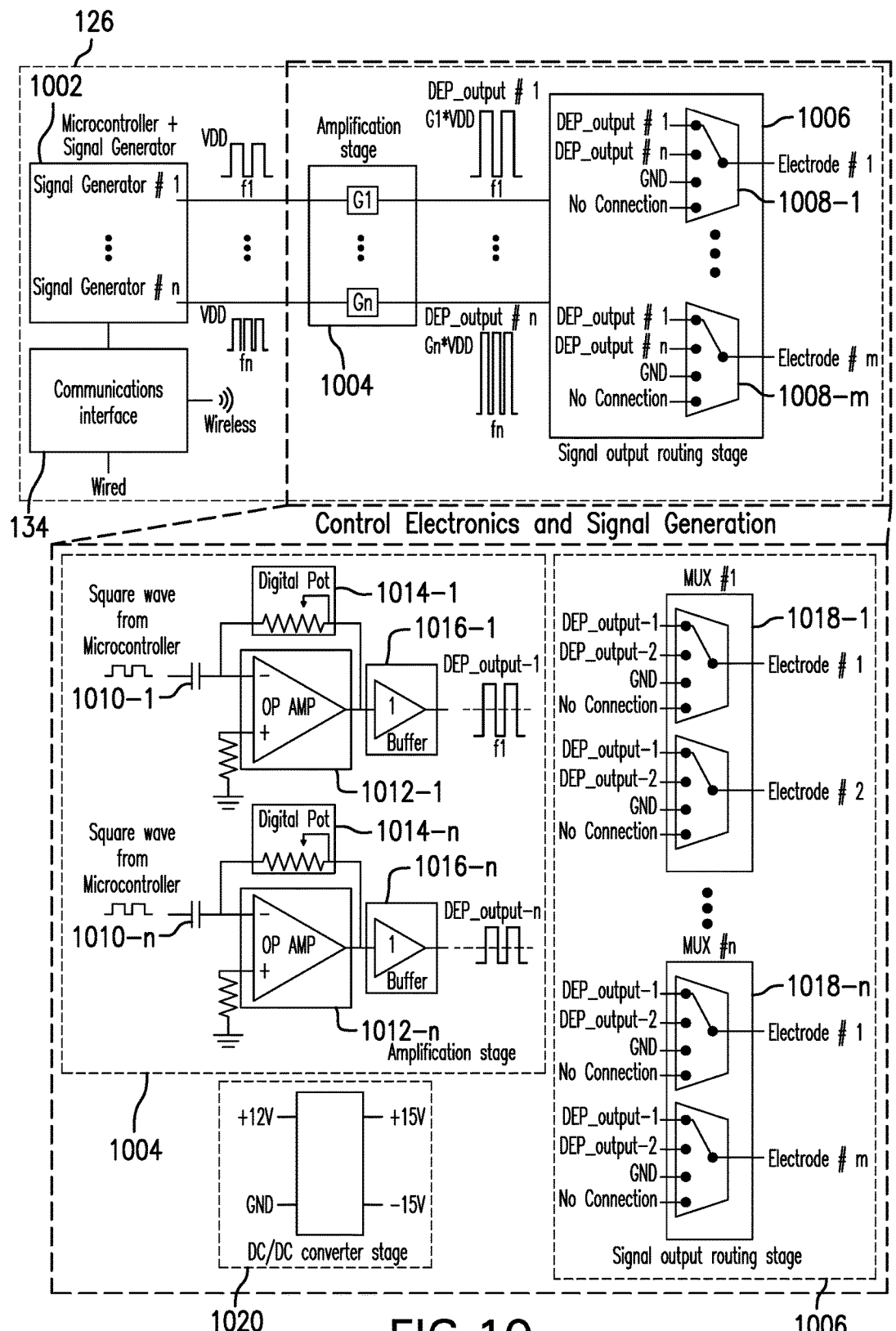
FIG. 10 shows a circuit diagram of an amplification stage suitable for DEP signal generation, in accordance with an aspect of the invention.
Figure 11:
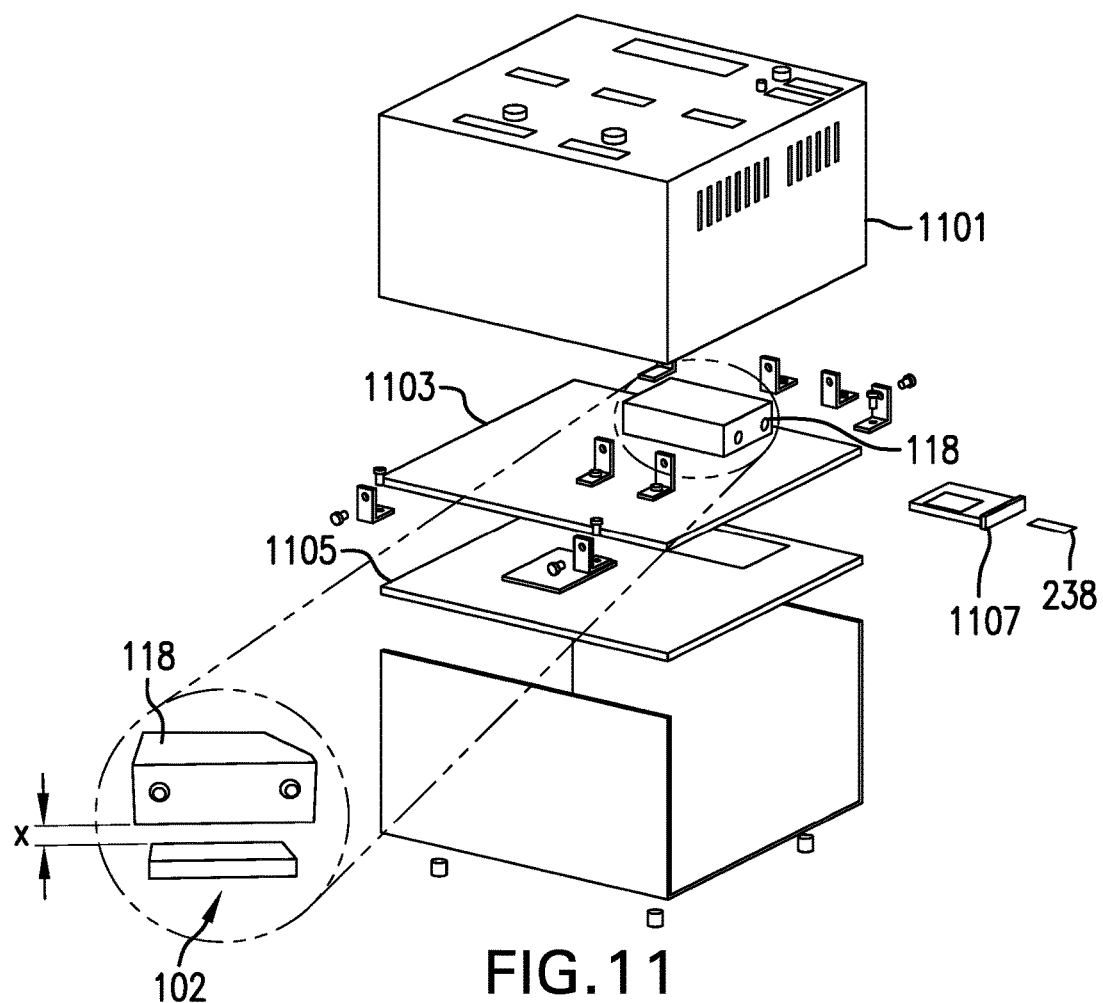
FIG. 11 shows an exploded view of the first embodiment of the system, in accordance with an aspect of the invention.

FIG. 10 shows a circuit diagram of an amplification stage suitable for use in a first exemplary embodiment, while FIG. 11 shows an exploded view of the first exemplary embodiment. In this first exemplary embodiment, the modules include optical and detection module 118. This can be implemented, for example, as a commercial fluorescence measurement module by from Qiagen N.V. of Hilden, Germany, or other supplier, including light sources (e.g., LED), lens(es), filters and a photo detector. A custom made version can also be applied in this case such as in the example of FIG. 5. Optical module output is in the form of a single voltage value proportional to the integrated fluorescence intensity over the photo detector measurement area. Mechanical module 102 handles chip-reader interface needs to accommodate the need for complete darkness during measurement—thus, the microfluidic chip is entirely inside the reader in this example. A push-to-click mechanism easily secures the chip and provides alignment with the DEP area and optical module 118 (for instance, using the well-known ExpressCard/34 interface slot as an interface solution). In a non-limiting example, the box 1101 is 20.5 cm wide×19 cm deep×10.5 cm high. An internal plastic division 1103 separates the prototype board 1105 from the chip and optical module. In this non-limiting example, the chip drawer 1107 is 3.4 cm wide×0.3 cm high×6.0 cm deep. The distance X from the microfluidics chip to the optical module is 3 mm, the internal plastic division 1103 is 3.5 cm from the case bottom, and the internal plastic division 1103 measures 19 cm wide×15.5 cm deep.

In a non-limiting example, the Electronics and Data (signal) processing modules 110, 126, 1105 are integrated into a single unit and employ a CY8CKIT-001 PSoC Development Kit common development platform available from Cypress Semiconductor Corporation, San Jose, Calif., USA, as rapid prototype of signal generation/control/logic analysis of the fluorescence reader. This is combined with the amplification stage described in FIG. 10. Components include an AC signal generator (providing sinusoidal wave, square wave, and the like) with variable frequency (by varying the signal generator inside the microcontroller or varying the oscillator frequency) to be applied to electrodes in the microfluidic chip in order to generate and control the DEP forces at various locations along the microchannel. Reader prototype control handles set-up, fluorescence analysis options, and the like. Fluorescence signal processing and display in LCD is also provided. The communication module can be wired (e.g. serial standards, such as $I^2C$, SPI and UART) or wireless (e.g. such as Bluetooth). The interface between the microfluidic chip and electronics can be provided, for example, through a discrete socket component.

Referring to FIG. 10, a suitable amplification stage 1004 executes variable amplitude (by varying the G gain in the amplification stage) to be applied to the electrodes in the microfluidic chip in order to generate and control the DEP forces at various locations along the microchannel. This stage executes the electrode configuration, so each electrode can be changed individually (signal output routing stage). Signal processing stage 126 includes communications interface 134 (wired and/or wireless) with a microcontroller 128, 130 as discussed above and signal generator 1002. Signal generator 1002 generates 1 through n different signal waveforms. These are supplied to the amplification stage 1004 which includes n individual amplification stages with gains G1 through Gn, in turn providing n amplified output waveforms to the signal output routing stage 1006. Signal output routing stage 1006 includes m multiplexers 1 through m with outputs connected to the m electrodes. Each multiplexer has as its selectable inputs ground, no connection and DEP output 1 to DEP output n. Details are shown at the bottom of the figure. The n individual amplification stages G1 through Gn each include a capacitor 1010-1, 1010-*n* coupled to the negative input of an operational amplifier (op amp) 1012-1, 1012-*n* which has its positive input grounded; a digital potentiometer 1014-1, 1014-*n* providing feedback from the output of the op amp back to the negative input, and a buffer 1016-1, 1016-*n* at the op amp output. The corresponding outputs are DEP_output_1 through DEP_output_n.

These outputs can be selectively applied to the appropriate electrodes via the signal output routing stage 1006. Please note that the multiplexers 1008-1 thru m in the upper part of the figure are a generalized depiction, while the multiplexers 1018-1 thru n in the lower part of the figure represent a particular exemplary implementation used in the first exemplary embodiment. Thus, in a general case, there can be from one up to n DEP signal generators, with one up to m electrodes. In the specific first exemplary embodiment, there are only two DEP signal generators; thus, at the top, each multiplexer has inputs 1, n, ground, no connection, while at the bottom each multiplexer has inputs 1, 2, ground, no connection.

DC/DC converter stage 1020 provides the symmetric voltage source necessary for the DEP amplification stage 1004. In this example, it has +12 V as input and ground, and provides as output +/−15 V.

Second Exemplary Embodiment

FIGS. 12-15 show various views of a second exemplary embodiment of a system, in accordance with an aspect of the invention. In the second embodiment, the commercial optical module is replaced by a customized setup including a CMOS or CCD image sensor for optical detection (fluorescence or colorimetric) with spatial resolution for more advanced image processing of the detection area and more quantitative analysis; a light source; various lenses; and filters. In one configuration, the device is customized to be used with opaque microfluidic chips such as those manufactured on silicon substrate. Such configuration implies illumination and detection from above the chip and a minimum distance between the chip and the image sensor. The magnification can be customized for the application (by way of example and not limitation, 100-120×). Moving the stage in three dimensions for focus and in-plane alignment is also provided, for better image acquisition, in at least some instances. Data can be sent to a mobile device (e.g., smart phone, tablet) or computer using a wireless interface (e.g.: Bluetooth, NFC, Wi-Fi), for visualization and analysis.

Figure 12:
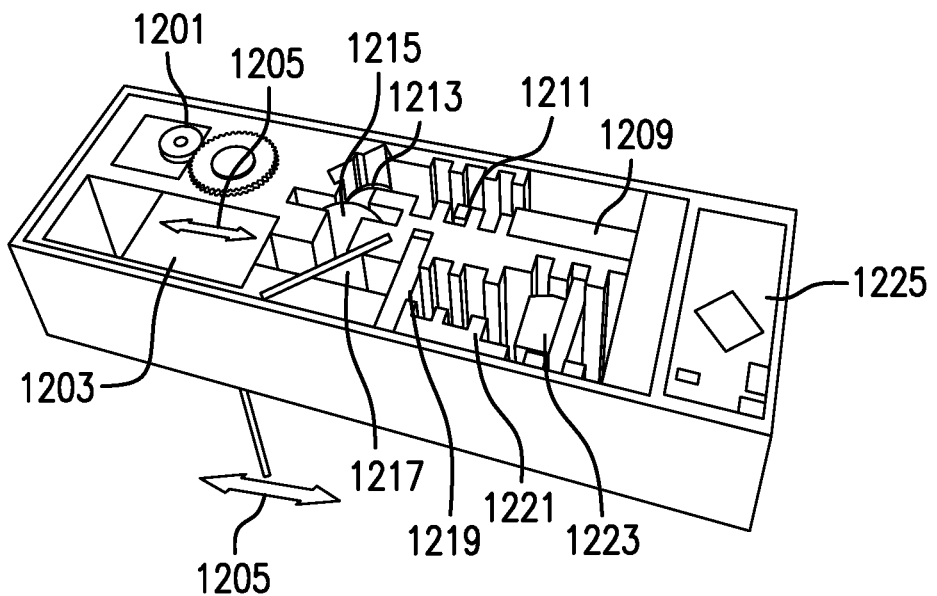
FIGS. 12-15 show various views of a second embodiment of a system, in accordance with an aspect of the invention.
Figure 13:
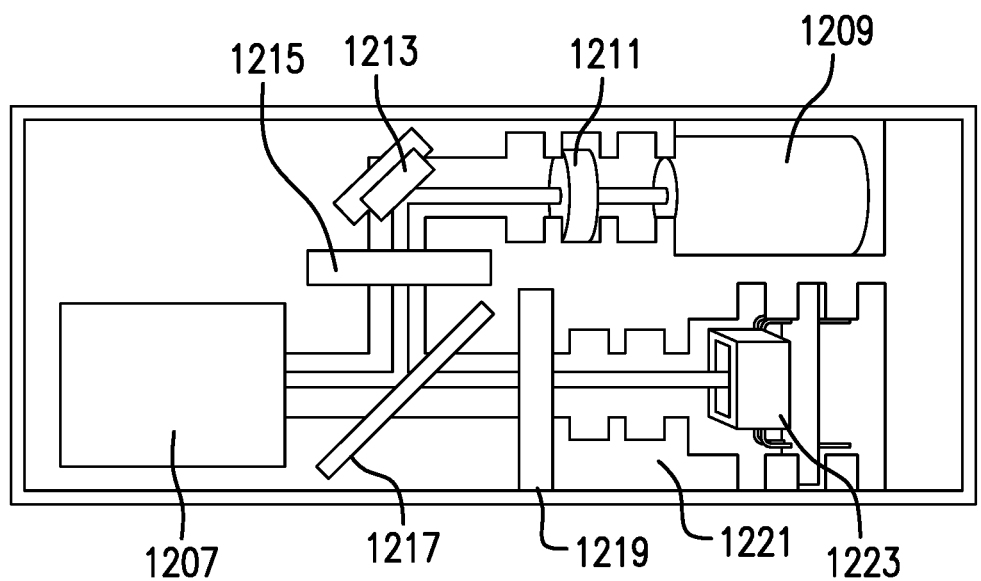
Figure 14:
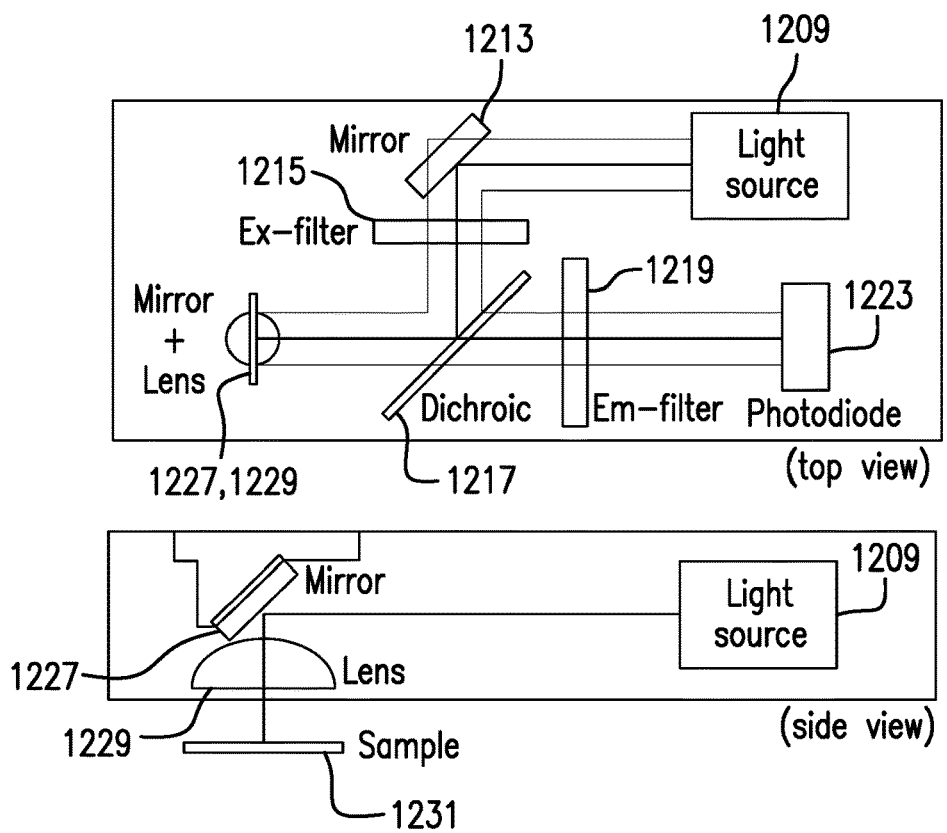
Figure 15:
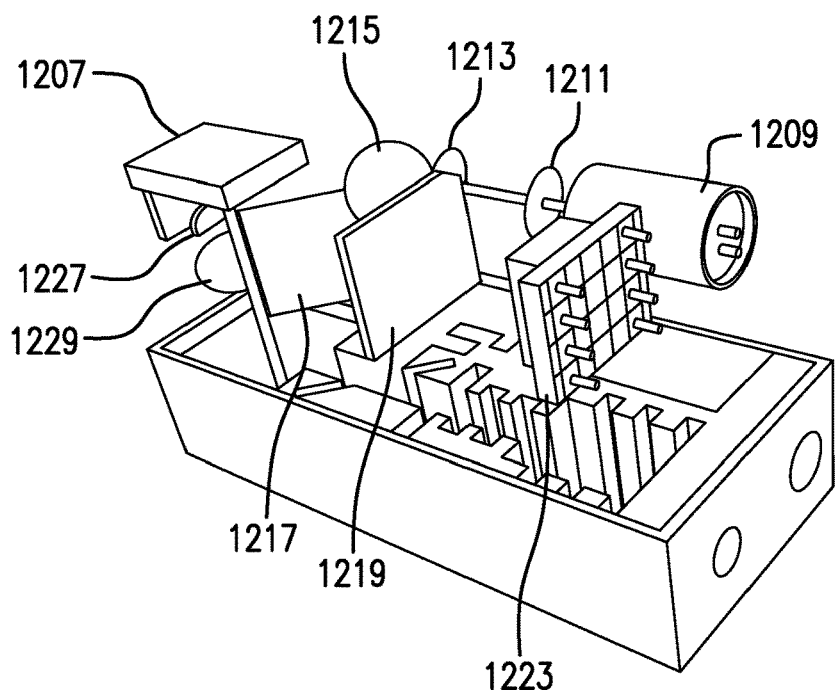
Figure 16:
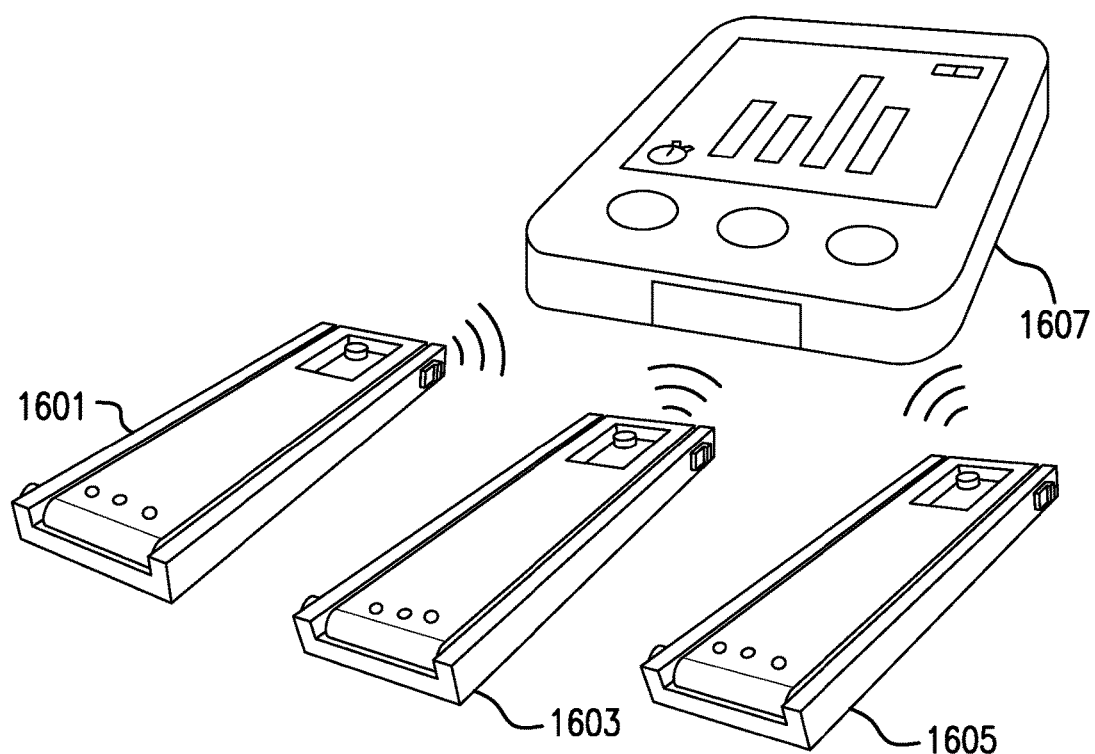

Several types of custom optical module can be employed; for example, one with analog interface and fixed beam, as in FIGS. 13 and 15, and another with digital interface and beam scanning, as in FIG. 12. In the embodiment of FIG. 12, note stepper motor 1201 providing linear motion symbolized by arrows 1205 (e.g., 1-2 cm of beam scanning); mirror and lens housing 1203; light source 1209 (LED or laser); optional collimating lens 1211; mirror 1213; excitation filter 1215; dichroic mirror 1217; emission filter 1219; optional lens rack 1221; and photodiode or camera 1223. Note also microcontroller and USB interface 1225. The analog interface and fixed beam version shown in FIGS. 13 and 15 is generally similar, except its mirror and lens housing 1207 is fixed and it omits interface 1225. As seen in FIG. 15, housing 1207 includes mirror 1227 and lens 1229. Housing 1203 can house a similar lens and mirror (not shown to avoid clutter). FIG. 14 is a schematic showing elements common to both versions, in top and side views (labeled). The sample is seen at 1231 and is under housing 1203 or 1207 as the case may be.

Non-limiting exemplary dimensions include 6 cm length, 2.5 cm width, and 1.2 cm height.

In some instances, a plastic platform is provided with several vertical slots to provide distance adjustments, capable of holding the various optical elements (LED, lens, mirror, filter, photodetector or CCD sensor) and built using, for example, a 3D printer. In some cases, the plane of the sample and the plane of the photodetector are not parallel, requiring an additional mirror to bend the light, but this is not a limitation and the sample and detection planes can be made parallel in other cases. This optical module could, in some cases, be combined with aspects of the electrical, mechanical, and signal processing modules described in with regard to the first exemplary embodiment.

Third Exemplary Embodiment

Figure 17:
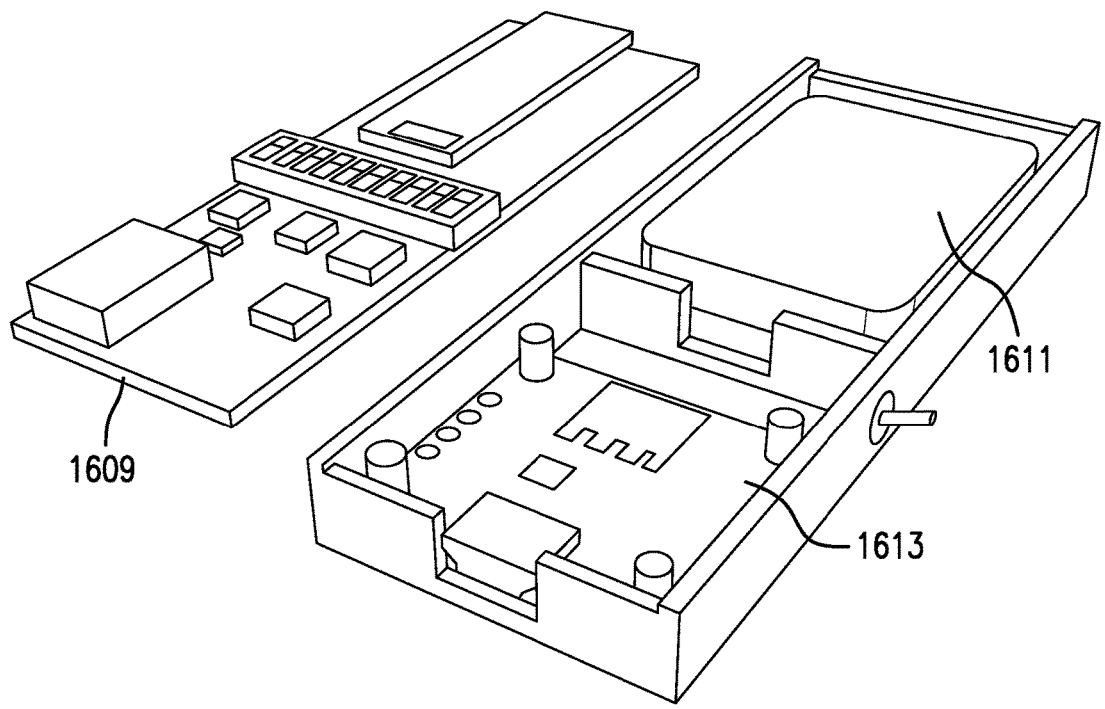

FIGS. 16-26 show various views of a third embodiment of a system, in accordance with an aspect of the invention. This embodiment provides multiplexing capabilities. Several DEP cartridges 1601, 1603, 1605 trap the beads and give a signal when the chip is ready for detection. The microfluidics chip is connected to the DEP cartridges using spring-loaded contacts. The reader is not occupied during the DEP trapping. Wireless communications can be established for base station 1607 to communicate with multiple cartridges 1601, 1603, 1605. Each cartridge 1601, 1603, 1605 can include a circuit board with DEP electronics 1609, as seen in FIG. 17, as well as an associated battery 1611 and battery electronics 1613 underneath.

In this third exemplary embodiment, the electrical module is integrated with the chip platform and electrical connector to produce a stand-alone module for powering the electrodes. The AC signal generator can be controlled through a physical ON/OFF switch connected to the unit or using the capacitance liquid position detection described previously. This module communicates wirelessly with the signal processing unit to indicate when the chip is ready for detection, being attached to the base station 1607 using a tray mechanism, similar to the folding frame and detection module 118, described in FIG. 4, FIG. 5 and FIG. 7. This unit can be used under a conventional microscope or combined with the optical and signal processing modules described in the first exemplary embodiment to provide the complete solution, flexible enough to be applied on these two fluorescence measurements solutions.

In at least some cases, the third exemplary embodiment can employ a high density connector prototype. In this aspect, electrical interfacing via spring-loaded contacts increases the number of electrical contacts, keeping the chip size small, and providing approximately three times more contacts for the same footprint, as compared with the a card edge interface, such as Micro SD. Mechanical compression to a Poly(methyl methacrylate) (PMMA) cover secures the chip and an opening allows liquid loading and fluorescence/colorimetric analysis.

Figure 18:
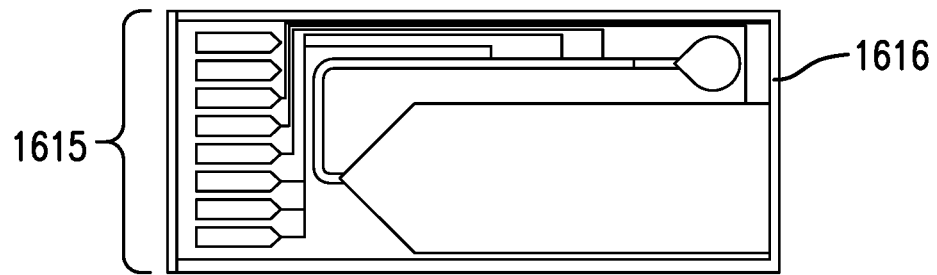
Figure 19:
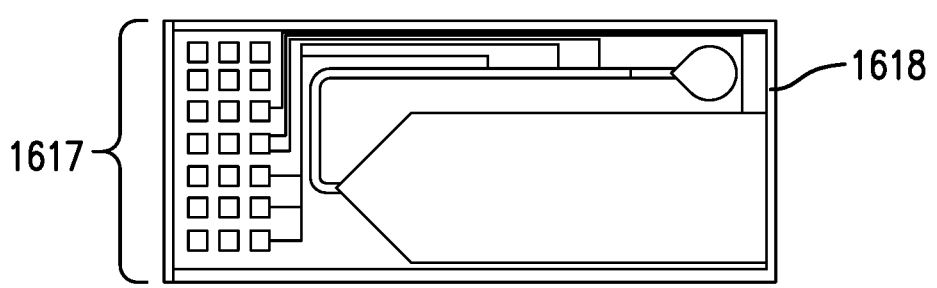
Figure 20:
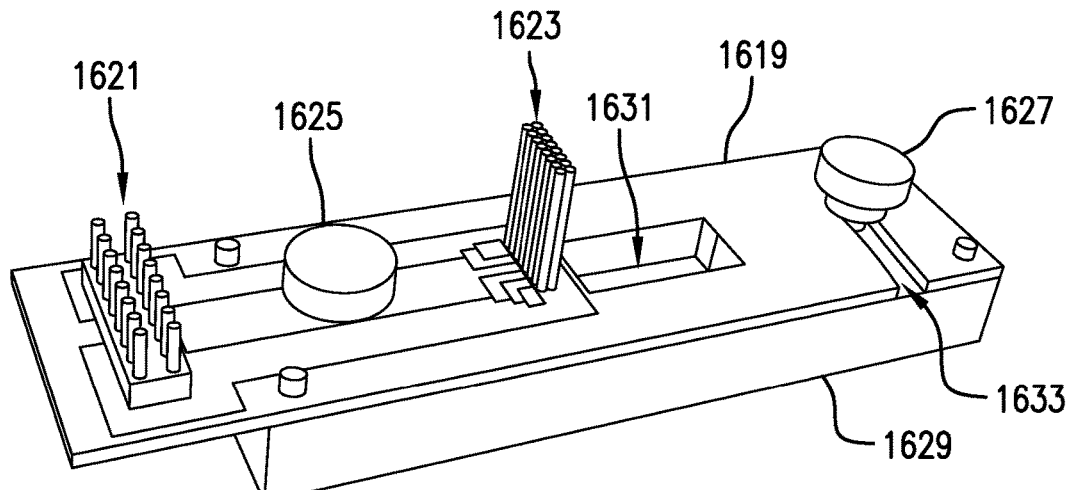
Figure 21:
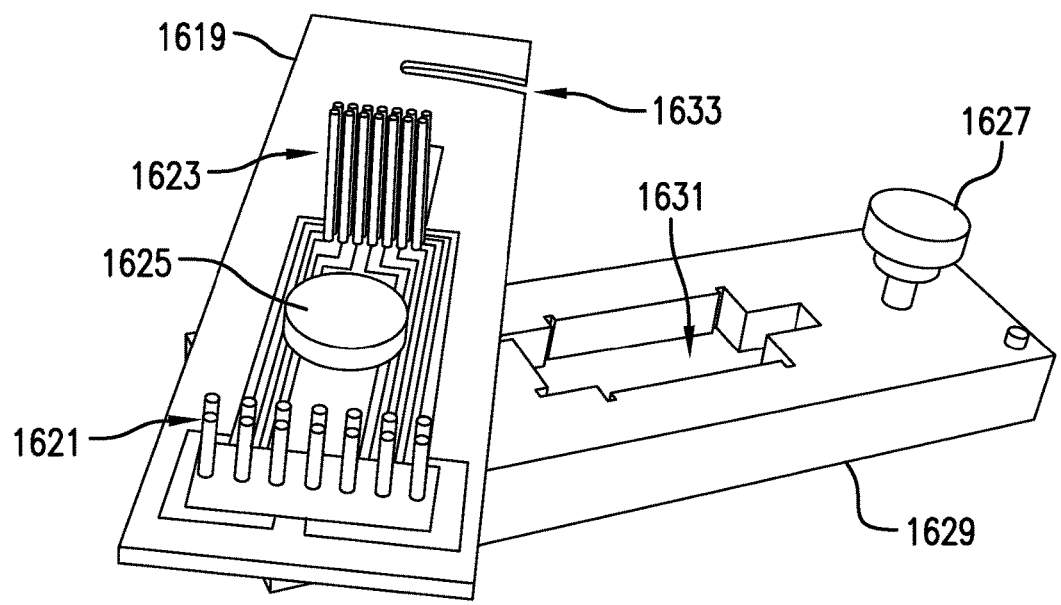
Figure 22:
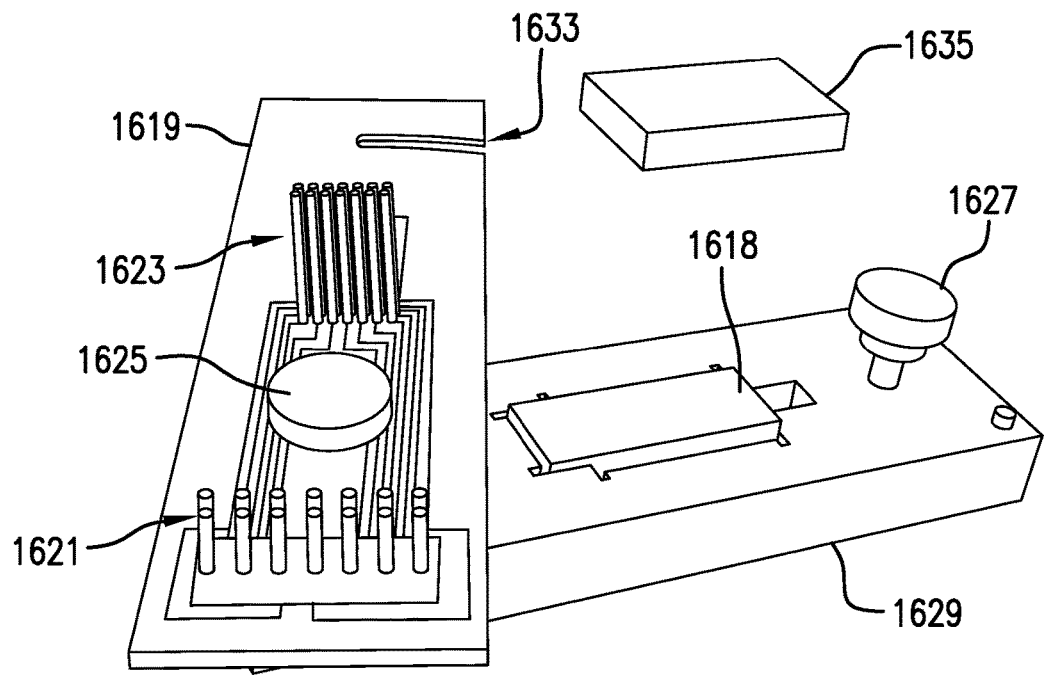
Figure 23:
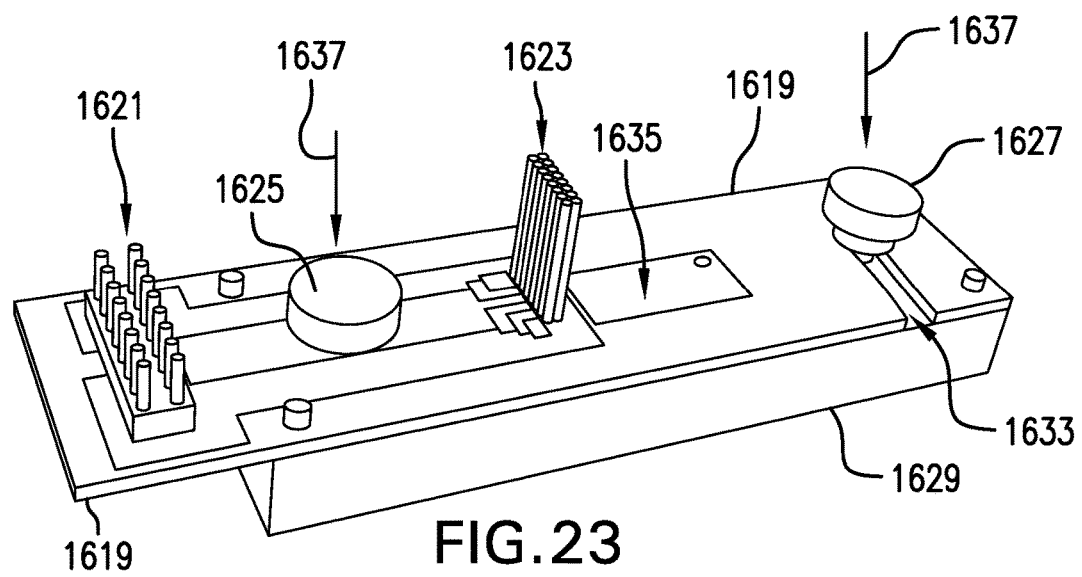

FIG. 18 shows a chip 1616 with a standard Micro SD card-edge connector with eight contacts 1615 in an approximately 4 mm×9.4 mm area. FIG. 19 shows a chip 1618 with an exemplary high-density card-edge connector with twenty-one contacts 1617 in an approximately 4 mm×9.4 mm area. FIG. 20 shows a printed circuit board (PCB) 1619 on an aluminum base 1629, pivoting about a first screw 1625 and secured by a second screw 1627 in slot 1633. Note chip-receiving cavity 1631 accessible through a corresponding hole in the PCB, as well as standard connector 1621 and Pogo pin array 1623. The hole in the PCB is smaller than the cavity, but big enough to allow optical analysis. In FIG. 21, screws 1625, 1627 are loosened and PCB 1619 pivots away from base 1629. In FIG. 22, chip 1618 is placed in cavity 1631 and transparent cover 1635 is brought proximate the chip. In FIG. 23, cover 1635 is placed over chip 1618, the PCB is pivoted back, and screws 1625, 1627 are tightened to provide compressive force symbolized by arrows 1637. In a non-limiting example, PCB 1619 can be 2.5 cm×9 cm, the standard connector 1621 can have two rows of seven pins with 2.54 mm pitch, and the Pogo pin array can have two rows of seven pins with 1.27 mm pitch.

Figure 25:
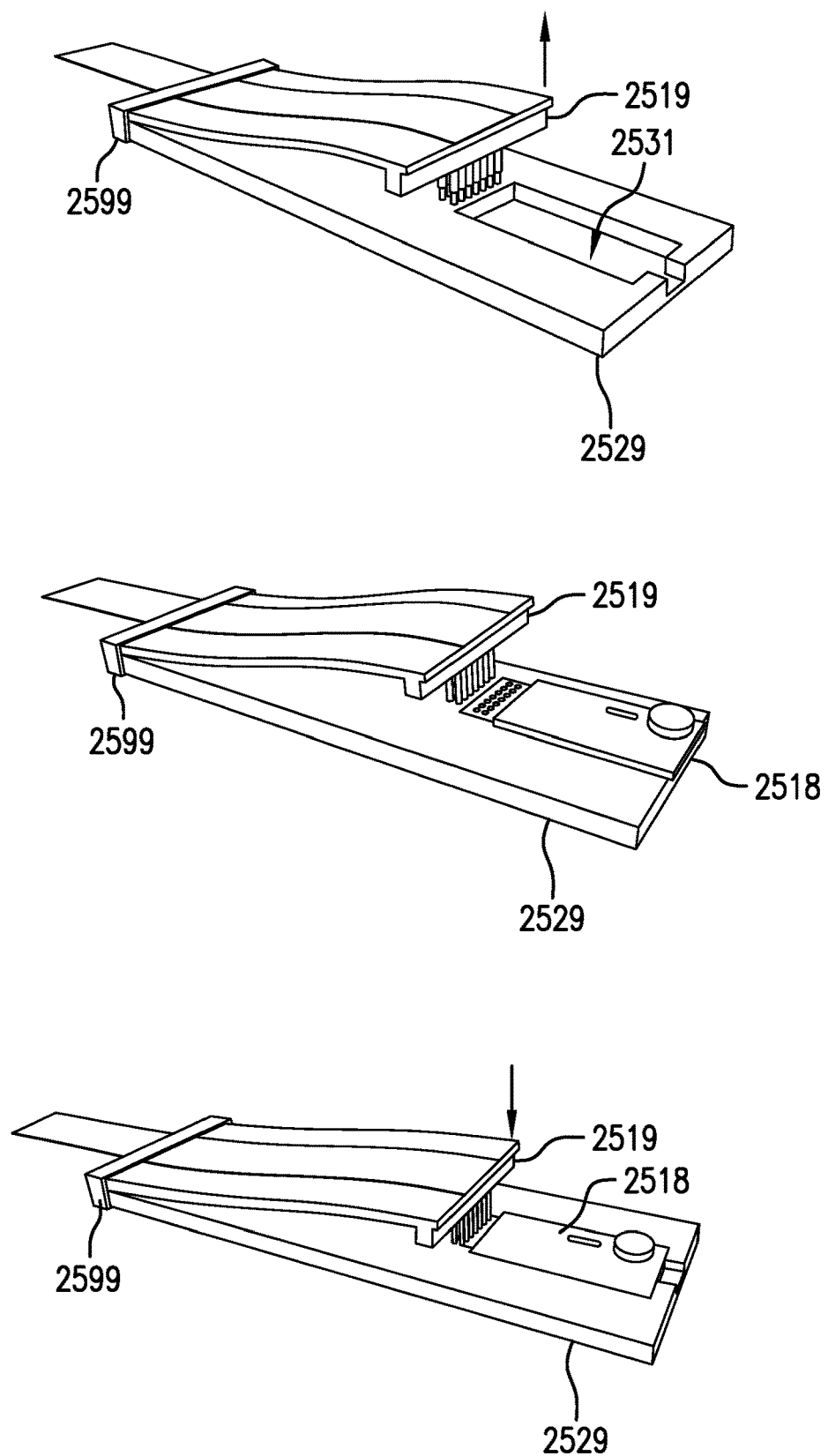
Figure 26:
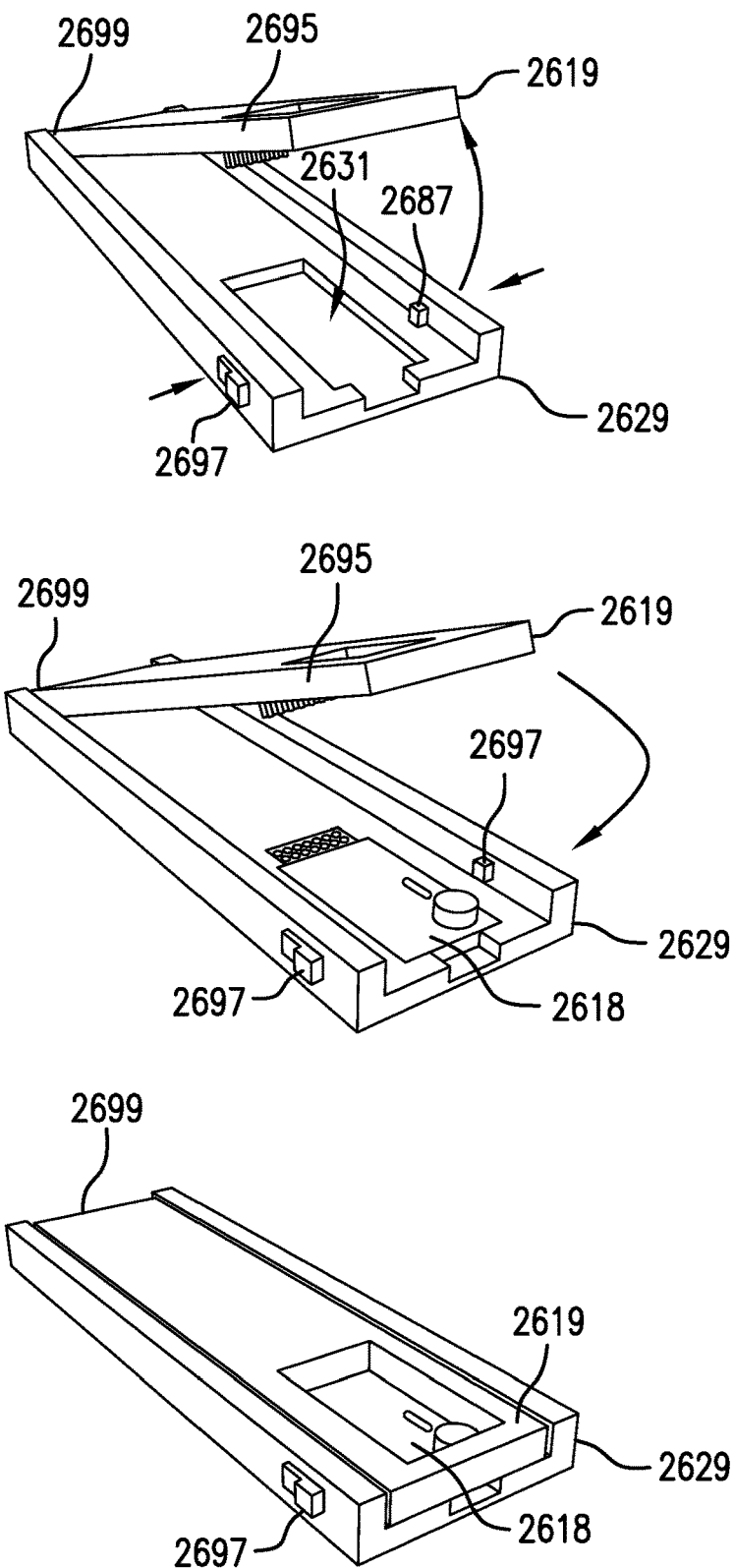
Figure 27:
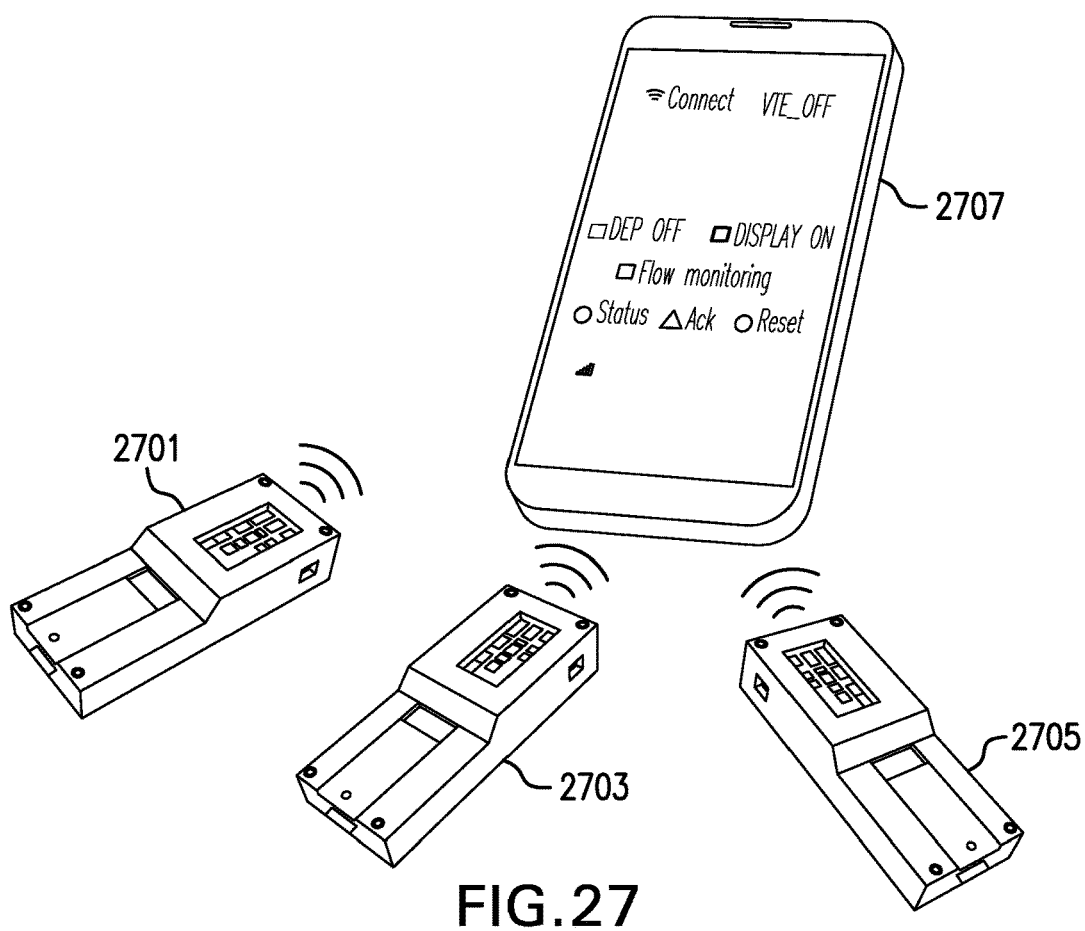
FIGS. 27-30 show various views of a fourth embodiment of a system, in accordance with an aspect of the invention.

Referring to FIGS. 24-26, this high density connector can be implemented in several different forms, such as slide, hinge or flexible mechanisms. FIG. 24 shows a sliding hinge mechanism wherein PCB 2419 is analogous to PCB 1619, and is joined to bottom portion 2429 (analogous to 1629) by four links 2499. Note chip-receiving cavity 2431 in bottom portion 2429, with a corresponding hole in the PCB 2419. An initial closed state is shown at the top. A pivoted-open state is shown in the middle. Chip 2418 (with any needed cover, not separately numbered) is placed in the cavity and the assembly is closed, in the bottom view.

FIG. 25 shows a flexible contact approach wherein a flexible top portion 2519 is joined to bottom portion 2529 (analogous to 1629) at a far edge 2599. Note chip-receiving cavity 2531 in bottom portion 2529. An initial state is shown at the top with the top portion being lifted. An open state is shown in the middle with chip 2518 (with any needed cover, not separately numbered) placed in the cavity. The assembly is closed, in the bottom view.

FIG. 26 shows a hinge lock mechanism wherein a top portion 2619 is joined to bottom portion 2629 (analogous to 1629) at a far edge 2699. Note chip-receiving cavity 2631 in bottom portion 2629. An initial state is shown at the top with the top portion being lifted. An open state is shown in the middle with chip 2618 (with any needed cover, not separately numbered) placed in the cavity. The assembly is closed, in the bottom view. Locking detents 2697 in the base can engage detents 2695 in the top.

Fourth Exemplary Embodiment

Figure 28:
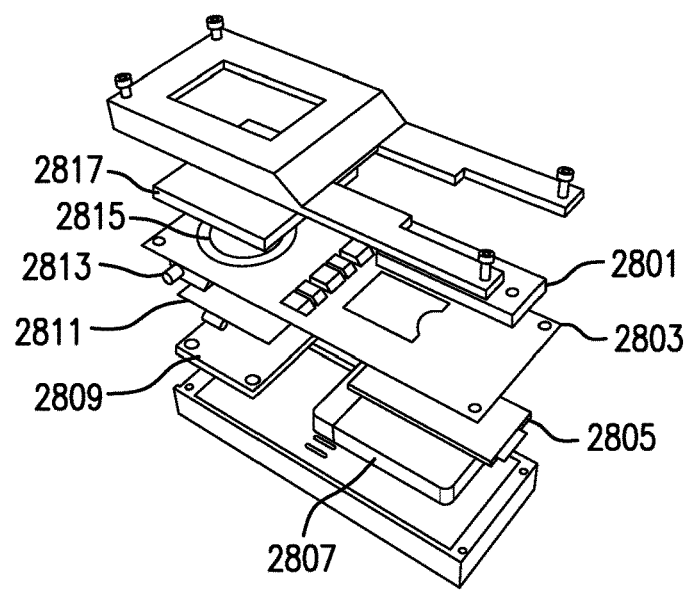
Figure 29:
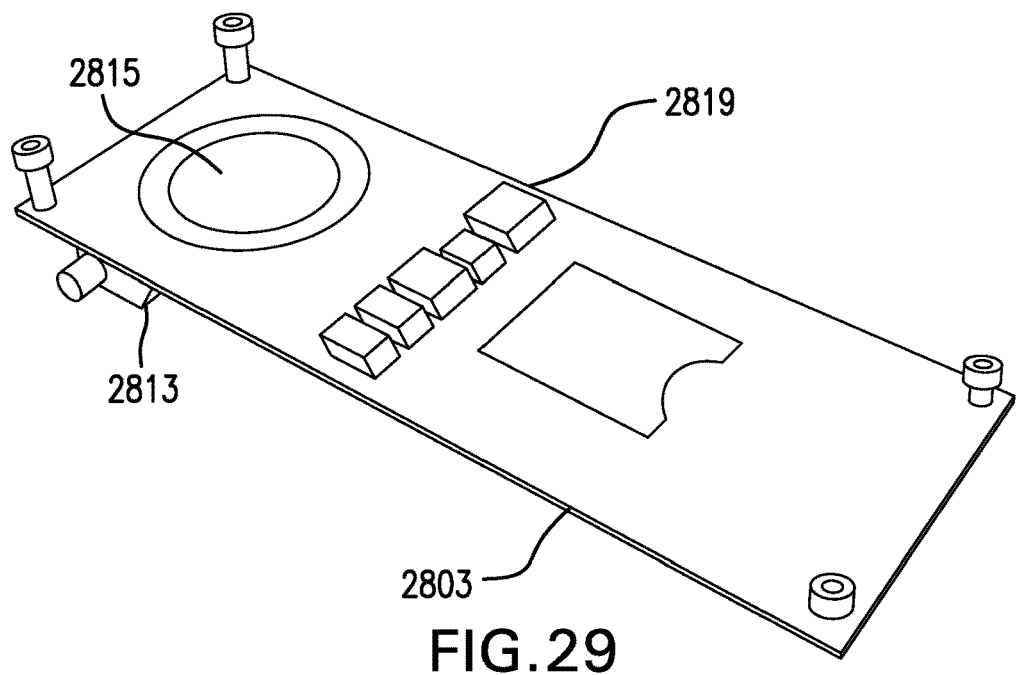
Figure 30:
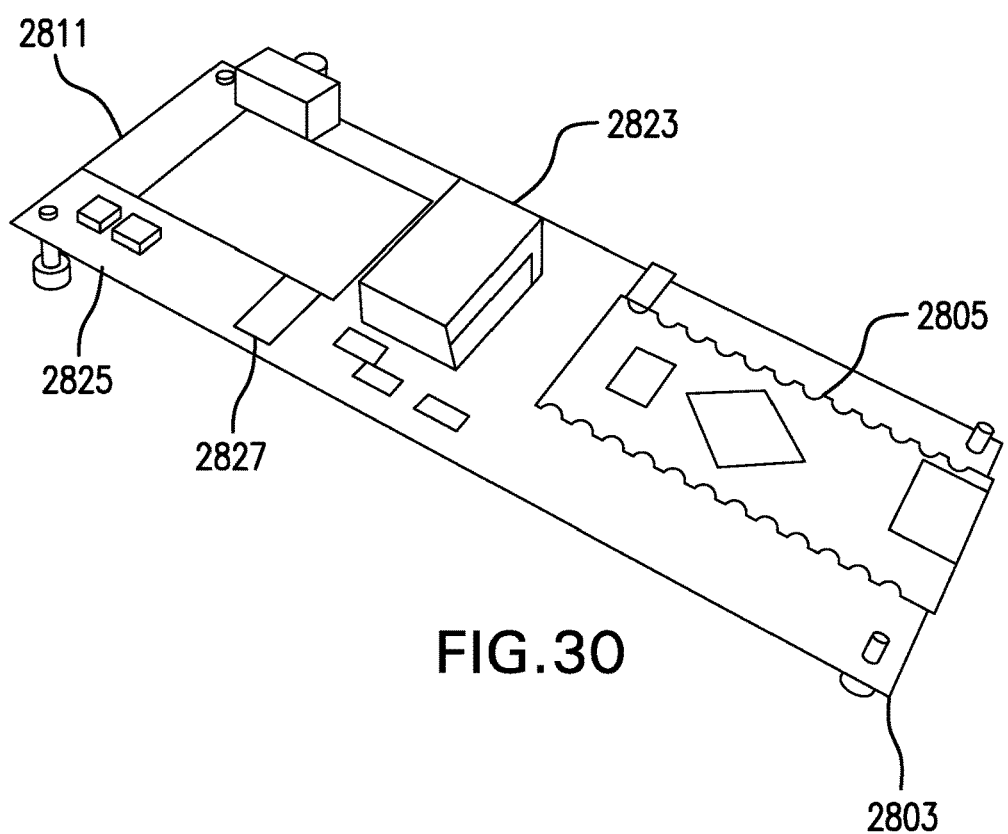

FIGS. 27-30 show various views of a fourth embodiment of a system, in accordance with an aspect of the invention. This embodiment is similar to the third exemplary embodiments, except that smart phone 2707 is used to control DEP cartridges 2701, 2703, 2705; capacitance measurements are used to track fluid flow inside the microchannels, and audio/visual feedback is provided both on the device and on the mobile phone, as well as chip presence detection. FIG. 28 shows an exploded view of an exemplary cartridge. Note microfluidic chip 2801, main board 2803, microcontroller 2805, LI-polymer battery 2807, battery charger and 5V regulator 2809, Bluetooth module 2811, on/off switch 2813, piezoelectric buzzer 2815, and organic light-emitting diode (OLED) display 2817. FIG. 29 shows a front side of main board 2803, with switch 2813, buzzer 2815 for sound notification, and DEP circuit 2819. FIG. 30 shows a back side of board 2803, with microcontroller 2805 (e.g., Arduino-compatible), Bluetooth module 2811, DC/DC converter 2823 (e.g. 5V input with +/−12 V output), 3.3 V regulator 2827, and 3.3 V/5 V level shifter converters 2825.

In the fourth exemplary embodiment a two way wireless communication channel exist between the electrical and chip platform module powering the electrodes and the signal processing and communications module, which can be in the form of a mobile device 2707. The AC signal generator ON/OFF switch can be remotely controlled from the mobile device automatically or through a user interface. This setup can be used under a conventional microscope or can be combined with an optical module as described with respect to the third exemplary embodiment.

Figure 31:
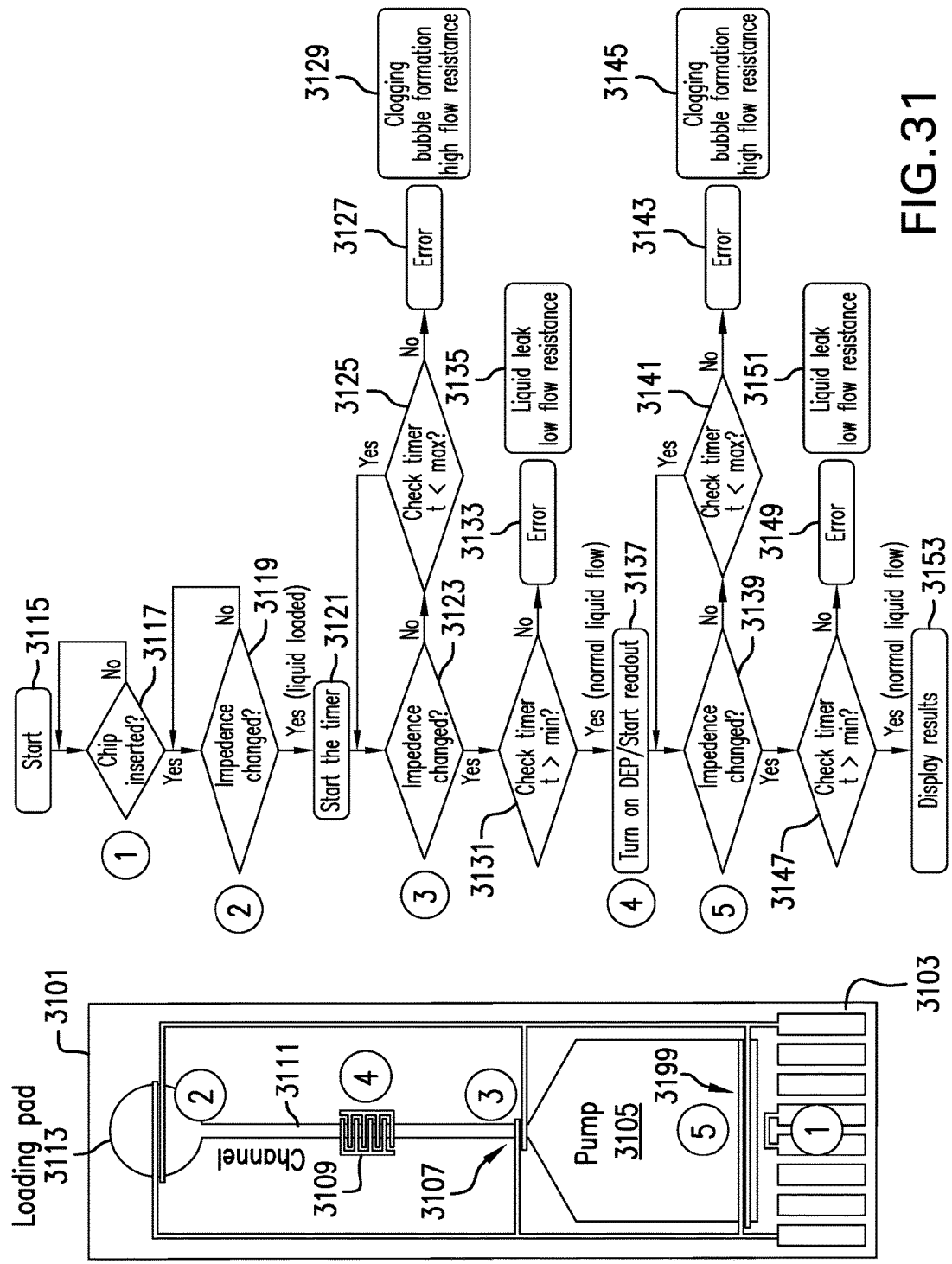
FIG. 31 shows a flow chart associated with the fourth embodiment of the system, in accordance with an aspect of the invention.

In the fourth exemplary embodiment, regarding liquid position detection, detection of chip presence and liquid position can be based on impedance (in this example, capacitance sensing). Typical common failures present in microfluidic devices (leakage, clogging, etc.) can be detected based on the time between each impedance measurement from specific check points. FIG. 31 shows a top view of a microfluidic chip 3101 including contacts 3103, capillary pump 3105, impedance detection electrodes 3107, DEP electrodes 3109, channel 3111, and liquid loading pad 3113. The large encircled numbers one through five key the top view of the microfluidics chip to corresponding portions of the flow chart. The flow chart begins at 3115. In decision block 3117, determine whether the chip is inserted (i.e., is there contact with contacts 3103). If NO, continue to check and wait until a chip is detected. If YES, proceed to decision block 3119 and determine whether there has been a change in impedance. If NO, continue to check. If YES, liquid has been loaded at loading pad 3113; start the timer in step 3121 to allow the liquid to fill up the microchannel 3111. In decision block 3123, again determine whether there has been a change in impedance (i.e.: microchannel 3111 is already filled up with the sample). If NO, proceed to decision block 3125 and determine whether the timer is less than a maximum predefined value. If not, there has been an error, as at 3127, such as clogging, bubble formation, and/or high flow resistance, as at 3129.

If decision block 3125 yields a YES, continue to check for impedance changes until timer expiration.

If decision block 3123 yields a YES, continue to decision block 3131 and determine whether the timer is greater than a minimum predefined value. If not, there has been an error, as at 3133, such as a liquid leak and/or low flow resistance, as at 3135.

If decision block 3131 yields a YES, there is normal liquid flow—proceed to step 3137, turn on the DEP and start the readout. Continue to decision block 3139. In decision block 3139, again determine whether there has been a change in impedance. If NO, proceed to decision block 3141 and determine whether the timer is less than a maximum predefined value. If not, there has been an error, as at 3143, such as clogging, bubble formation, and/or high flow resistance, as at 3145.

If decision block 3141 yields a YES, continue to check for impedance changes and/or timer expiration.

If decision block 3139 yields a YES, continue to decision block 3147 and determine whether the timer is greater than a minimum predefined value. If not, there has been an error, as at 3149, such as a liquid leak and/or low flow resistance, as at 3151. If YES, proceed to step 3153 and display (and/or output) the results.

Figure 32:
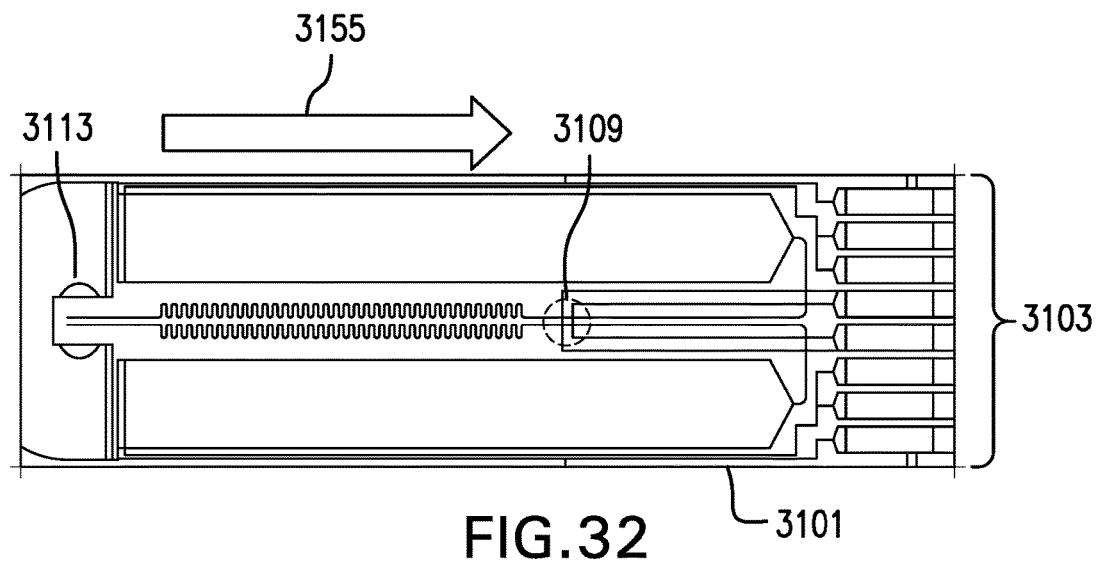
FIGS. 32 and 33 show a plan view and circuit diagram associated with testing aspects of the fourth embodiment of the system, in accordance with an aspect of the invention.

FIG. 32 shows an alternative view of microfluidics chip 3101 including contacts 3103, DEP electrodes 3109, and liquid loading pad 3113. The arrow 3155 shows flow as a function of time. Please note that in FIG. 31, there are two pairs of electrodes dedicated to flow detection, while in FIG. 32 there is only a pair of electrodes dedicated to DEP excitation.

Figure 33:
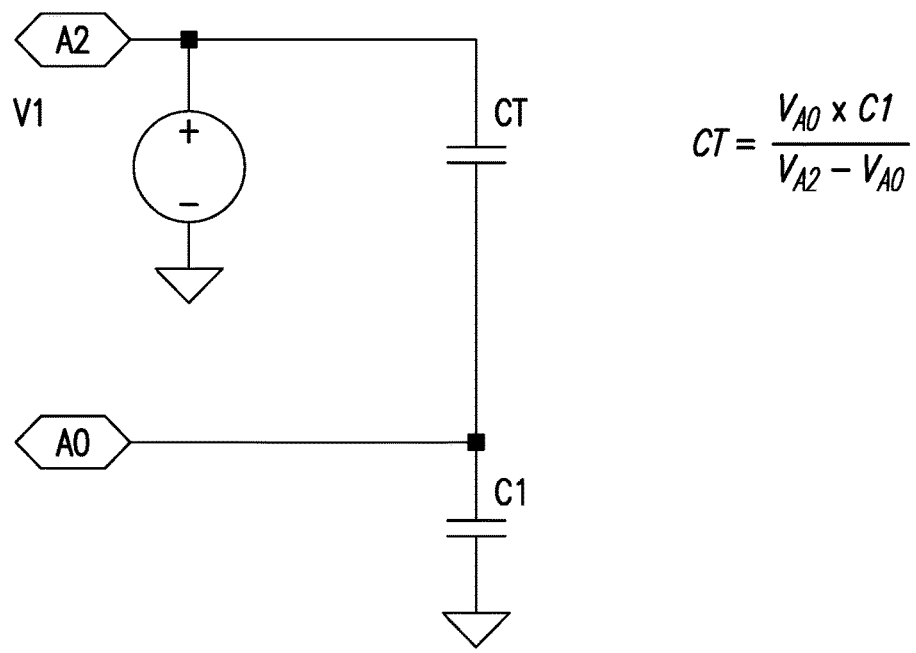

FIG. 33 shows a circuit diagram associated with testing aspects of the fourth embodiment of the system. CT is the capacitance under test (unknown), which is, in this case, the capacitance between the electrodes deposited in the microchannels (impedance detection electrodes 3107 in FIG. 31). CT will change when the channel is filled up with the liquid sample, compared to when it was filled with air. C1 is a stray capacitance (say, about 30 pF, typically). Voltage V1 is applied at A2. For example, A2 may have its voltage increase from 0V to 5V in about 5 ns. The voltage on A0 can then be measured after about 30 ns. CT is calculated as the voltage at A0 times C1, divided by the difference between the voltage at A2 and the voltage at A0. This is so because for capacitors in series, each holds the same charge Q; thus, CT times the voltage drop across it ($V_{A2}-V_{A0}$) equals C1 times the voltage drop across it ($V_{A0}$). The A0 node can be connected to any suitable microcontroller port that allows analog measurements.

Figure 34:
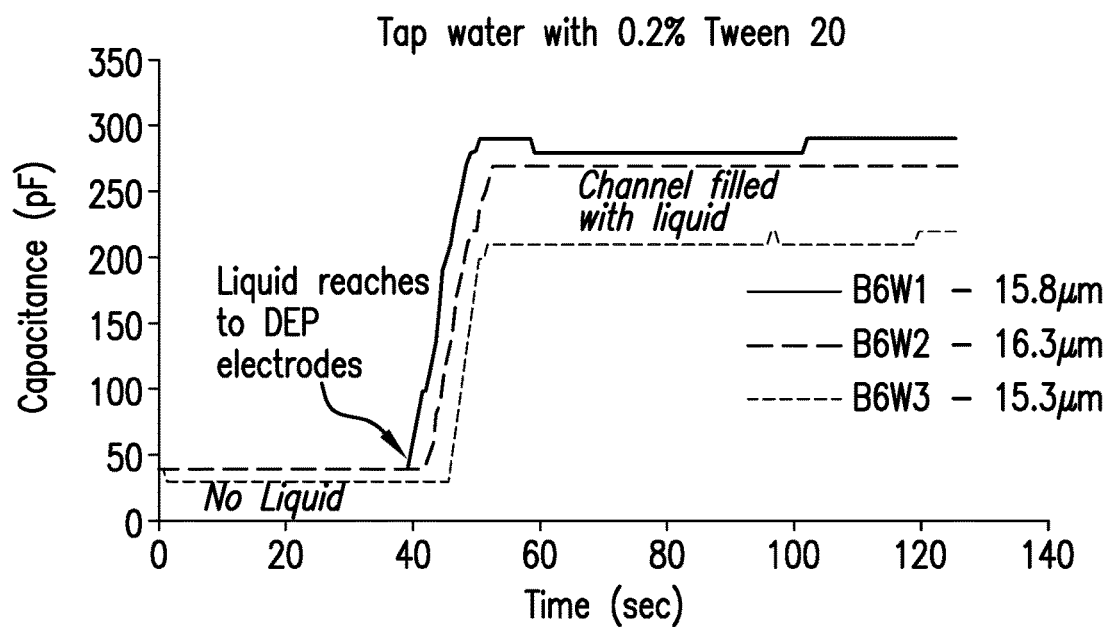
FIG. 34 shows a graph of capacitance versus time from the testing aspects of FIGS. 32 and 33, in accordance with an aspect of the invention.

FIG. 34 shows a graph of capacitance versus time from the testing aspects of FIGS. 32 and 33, in accordance with an aspect of the invention. In particular, FIG. 34 shows a typical variation of the measurement carried out by the impedance detection electrodes 3107 (CT) in time, after the sample is put in loading pad 3113.

The position of the fluid within the channel can be determined using dedicated electrodes positions at various checkpoints along the microchannel. These electrodes are connected to a microcontroller (e.g., Arduino) capable of measuring the capacitance between the contacts, which changes noticeably when the electrodes are covered by the liquid. This capacitance measurement is fed back wirelessly to the signal processing unit to determine the position of the fluid and control the AC signal generator ON/OFF switch remotely and accordingly, which can be done automatically following an algorithm without any intervention from the user.

Figure 35:
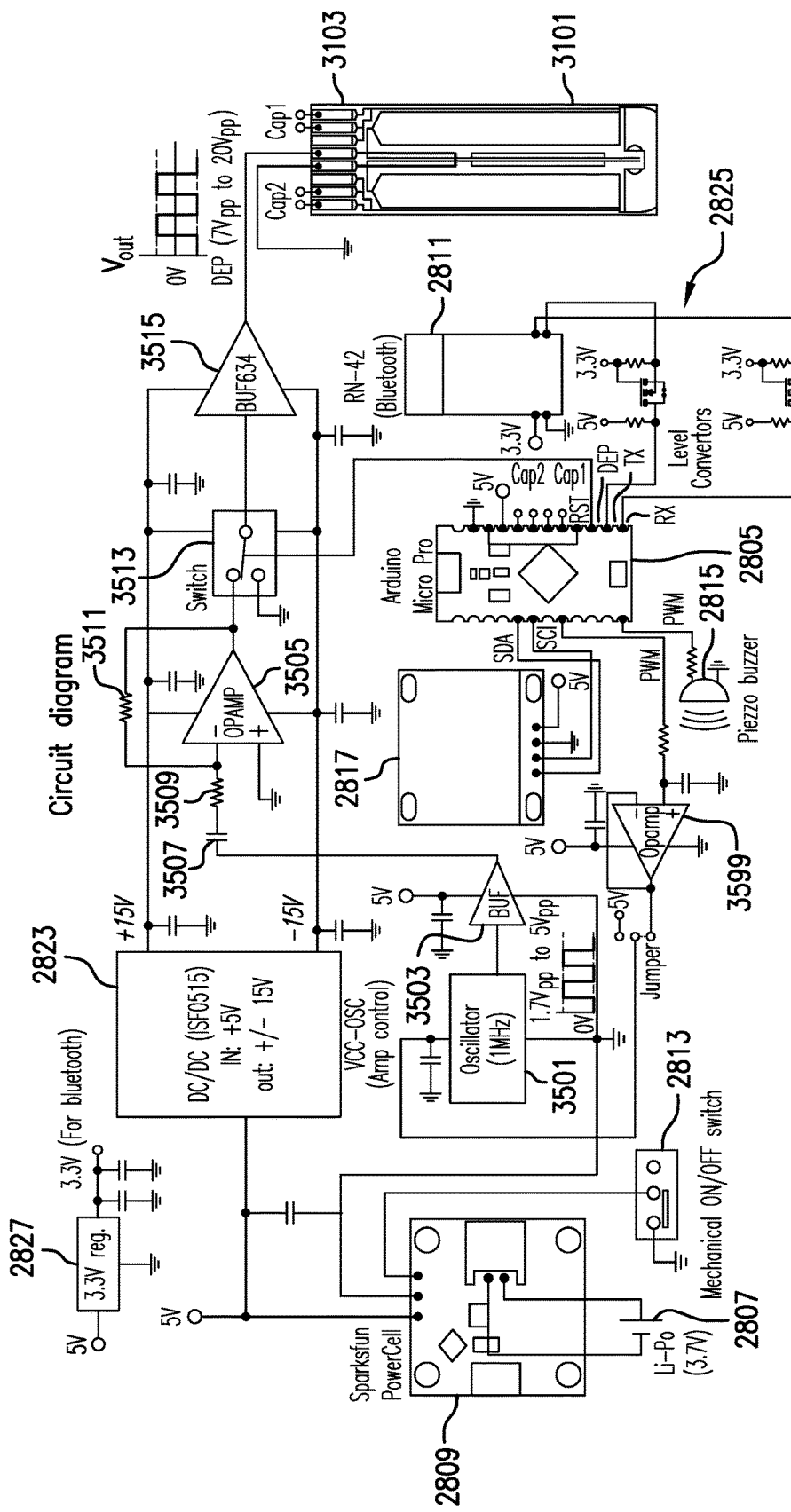
FIG. 35 shows a circuit diagram of a DEP cartridge of the third and fourth embodiment of the system.
Figure 36:
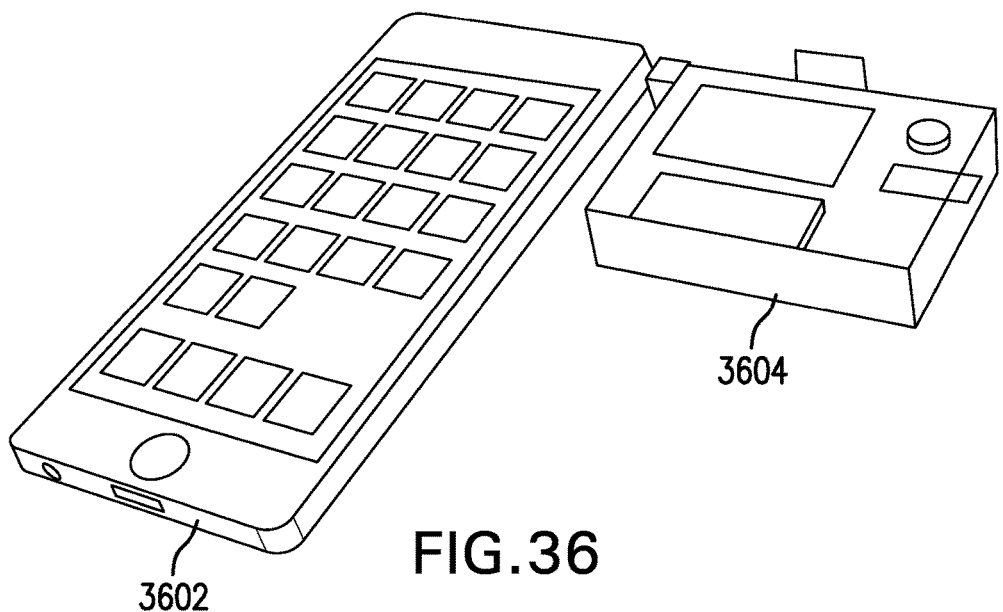
FIGS. 36-39 show various views of a fifth embodiment of a system, in accordance with an aspect of the invention.

FIG. 35 shows a circuit diagram of a DEP cartridge of the fourth embodiment of the system. The following tables show the ports and signals, and the voltage levels:

TABLE I

| Port | Signal |
| --- | --- |
| Bluetooth | Serial (receive (RX), transmit (TX)) |
| OLED Display | I²C (inter integrated circuit) (Serial Data Line (SDA) and Serial Clock Line (SCL)) |
| DEP Control | Pulse width modulation (PWM) amplitude control and digital on/off |
| Buzzer | Pulse width modulation (PWM) |
| Soft reset | Digital (active-low) |

TABLE II

| Voltage Level | Location |
| --- | --- |
| +3.3 V | Bluetooth |
| +3.7 V | Li-Po battery |
| +5 V | DEP oscillator, Arduino, OLED |
| +/−15 V | DEP circuit |

The output of oscillator 3501 is buffered in buffer 3503 and then fed to the input of op amp 3505 through capacitor 3507 and resistor 3509. The op amp is in negative feedback configuration, in which the gain is controlled with the ratio between resistors 3511 and 3509. The positive input of op amp 3505 is grounded. The output of op amp 3505 is also provided to switch 3513. When the DEP signal from the microcontroller 2805 is ON, switch 3513 connects the output of op amp 3505 to buffer 3515, which then provides the buffered output to the DEP contact of cartridge 3101. When the DEP signal from the microcontroller 2805 is OFF, switch 3513 grounds the input of buffer 3515. Op-amp 3599 is working as a unity gain buffer input for the oscillator 3501. The PWM signal will provide a variable voltage for the VCC oscillator input. In particular, one or more embodiments generate a DC voltage using PWM and a low pass filter (Resistor and Capacitor), then apply this voltage to the VCC of the oscillator. Because the oscillator generates a square wave varying from 0V to VCC, change the amplitude of the DEP signal by changing the VCC. Op-amp 3505 amplifies the signal using 3509 and 3511. Cap 3507 removes the DC offset, so that a square pulse is obtained, with an average value at 0V. Other elements in FIG. 35 are discussed elsewhere herein.

Fifth Exemplary Embodiment

Figure 37:
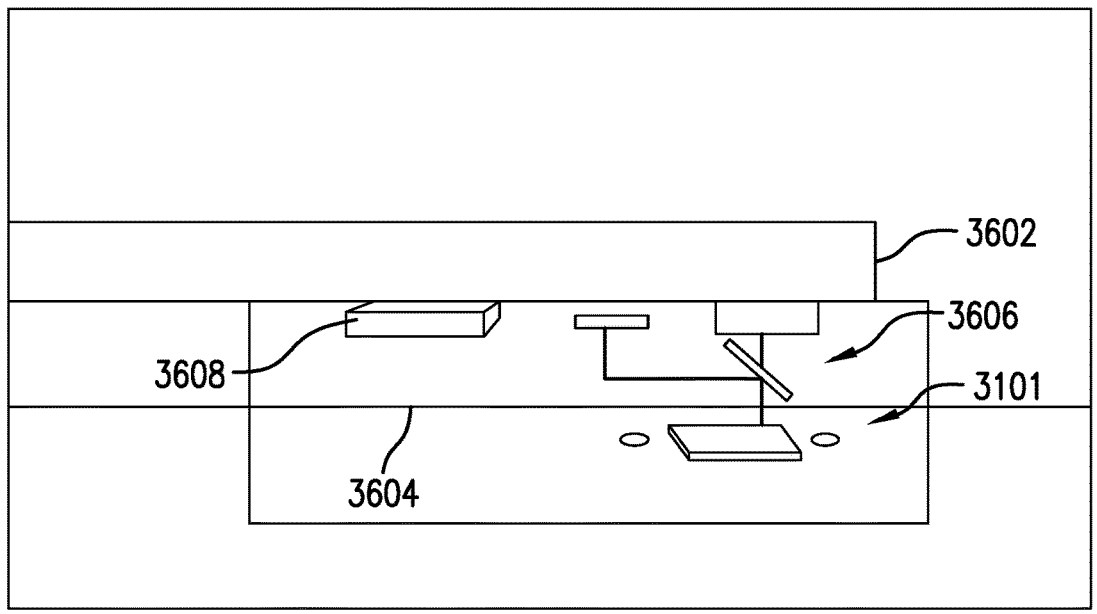
Figure 38:
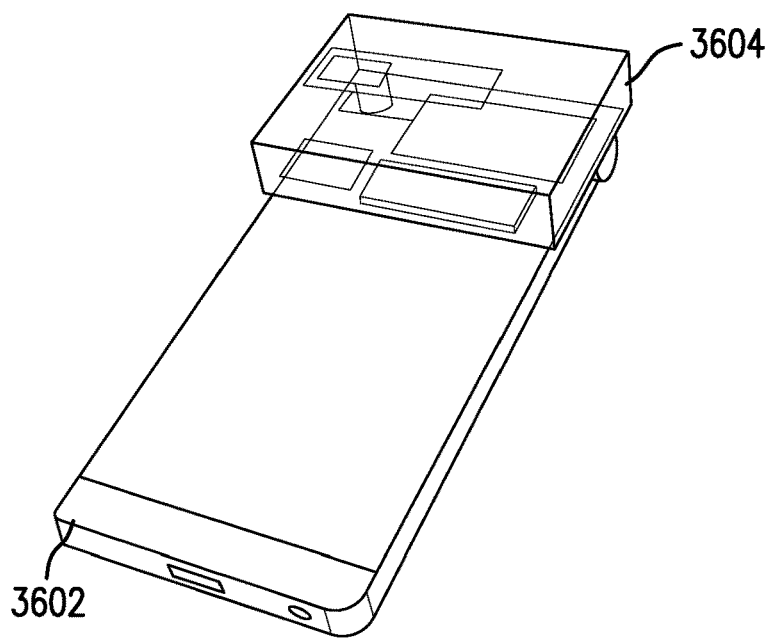
Figure 39:
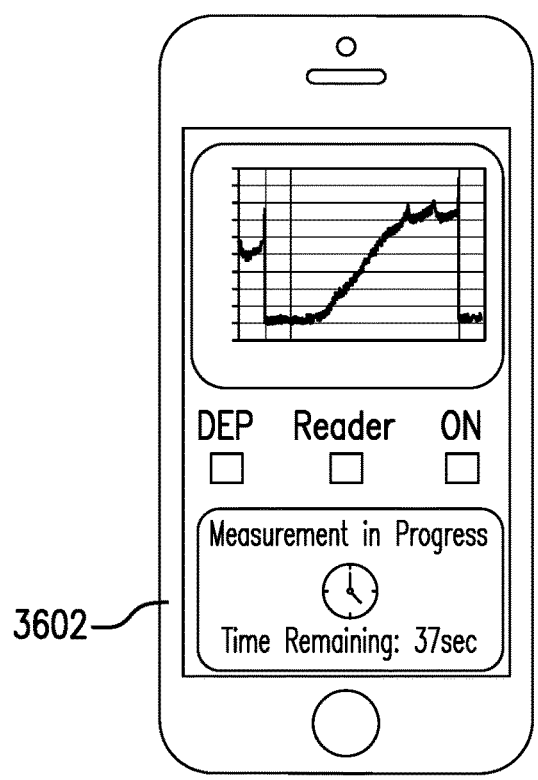

In a fifth exemplary embodiment, depicted in FIGS. 36-39, the entire system (mechanical, electronic and optical modules) is compactly integrated into a single attachment 3604 for a mobile device 3602. The image sensor and parts of the signal processing and communications module can exploit capabilities of current mobile devices, thereby reducing cost. For example, some modern mobile devices have dual or quad core central processing units (CPUs) with ~2 GHz and WiFi, Bluetooth, NFC, 3G, and/or LTE capability. This can lead to reduced cost and enhanced processing and user interface capabilities as well as providing an interface to cloud and data analytics. For example, a single compact highly integrated attachment to a mobile device is customized and built using low cost materials and integrating electrical, optical and mechanical modules only. The camera, computing and communication capability of the mobile device can be exploited as parts of the optical and signal processing and communication modules, respectively. As seen in FIG. 37, attachment 3604 includes a lens and mirror arrangement 3606 as described with regard to, e.g., FIGS. 12-15, which directs light to and from the chip 3101 and is located adjacent the camera lens (not separately numbered; see discussion of camera 8039 below) of the mobile device 3602. Element 3608 can include electromechanical and electro-optical functionality not provided by device 3602. FIG. 39 shows an exemplary screen shot including time remaining, buttons for DEP, readout, and on/off, and a voltage versus time graph.

This fifth exemplary embodiment relies on the ubiquity of smartphones, which could further employ an already existing computational infrastructure, such as cloud computer service, to allow data aggregation and analysis over several analyses, to obtain, for example, geographical disease distribution and outbreaks patterns. See the discussion of an exemplary "smart" device (FIG. 40 and accompanying text) and exemplary cloud environment (FIGS. 41-41 and accompanying text) that follow.

Exemplary Mobile Device

Figure 40:
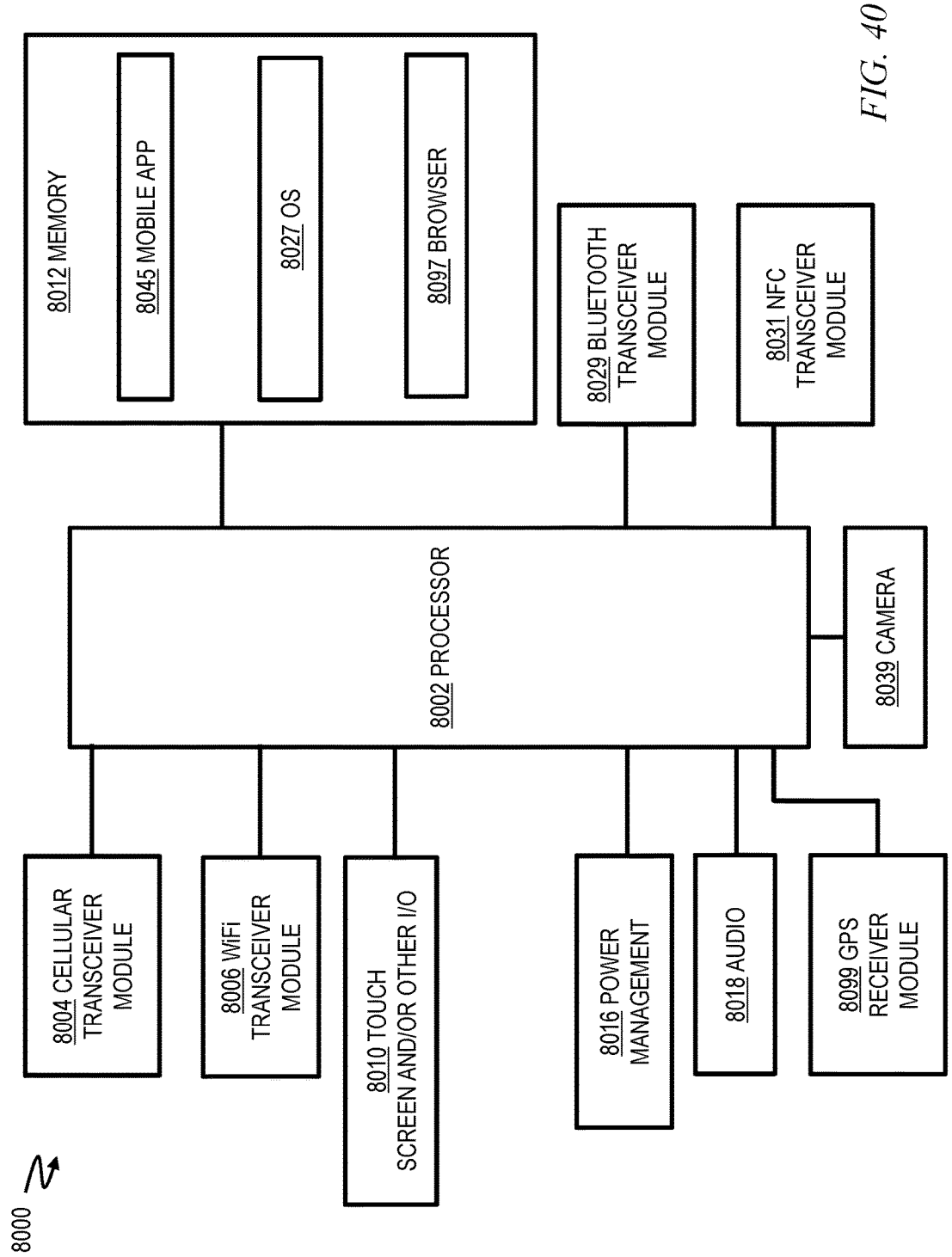
FIG. 40 is a block diagram of a "smart" phone or tablet computer useful in one or more embodiments of the invention.

FIG. 40 is a block diagram of an exemplary tablet computing device, netbook, laptop, mobile electronic device, or smart phone 8000 or the like. Unit 8000 includes a suitable processor; e.g., a microprocessor 8002. A cellular transceiver module 8004 coupled to processor 8002 includes an antenna and appropriate circuitry to send and receive cellular telephone signals, e.g., 3G or 4G. In some cases, a Wi-Fi transceiver module 8006 coupled to processor 8002 includes an antenna and appropriate circuitry to allow unit 8000 to connect to the Internet via a wireless network access point or hotspot. The skilled artisan will appreciate that "Wi-Fi" is a trademark of the Wi-Fi Alliance and the brand name for products using the IEEE 802.11 family of standards. In some cases, a Bluetooth transceiver module 8029 coupled to processor 8002 includes an antenna and appropriate circuitry to allow unit 8000 to connect to other devices via the Bluetooth wireless technology standard. In some cases, an NFC transceiver module 8031 coupled to processor 8002 includes an antenna and appropriate circuitry to allow unit 8000 to establish radio communication via near-field communications.

Operating system (OS) 8027 orchestrates the operation of unit 8000.

Touch screen 8010 coupled to processor 8002 is also generally indicative of a variety of input/output (I/O) devices such as a keypad, another type of display, a mouse or other pointing device, and so on, all of which may or may not be present in one or more embodiments. Audio module 8018 coupled to processor 8002 includes, for example, an audio coder/decoder (codec), speaker, headphone jack, microphone, and so on. Power management system 8016 can include a battery charger, an interface to a battery, and so on. Memory 8012 is coupled to processor 8002. Memory

8012 can include, for example, volatile memory such as RAM, and non-volatile memory such as ROM, flash, or any tangible computer-readable recordable storage medium which stores information in a non-transitory manner. Processor 8002 will typically also have on-chip memory.

A digital camera 8039 is coupled to processor 8002.

A GPS receiver module 8099 coupled to processor 8002 includes an antenna and appropriate circuitry to allow device 8000 to calculate its position by precisely timing the signals sent by GPS satellites high above the Earth. Corresponding software resides in memory 8012.

Note that elements in FIG. 40 are shown connected directly to processor 8002; however, one or more bus structures can be employed in one or more embodiments. Furthermore, elements shown as implemented in software may be implemented at least in part in hardware for speed, if desired.

Browser program 8097 in memory 8012 deciphers hypertext markup language (html) served out by a server (e.g. cloud computing node discussed elsewhere) for display on screen 8010 or the like.

Application 8045 in memory 8012 can be provided to control the embodiment of FIGS. 36-39.

Every instance need not necessarily have every feature depicted in FIG. 40.

Exemplary Cloud Computing Environment

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 41:
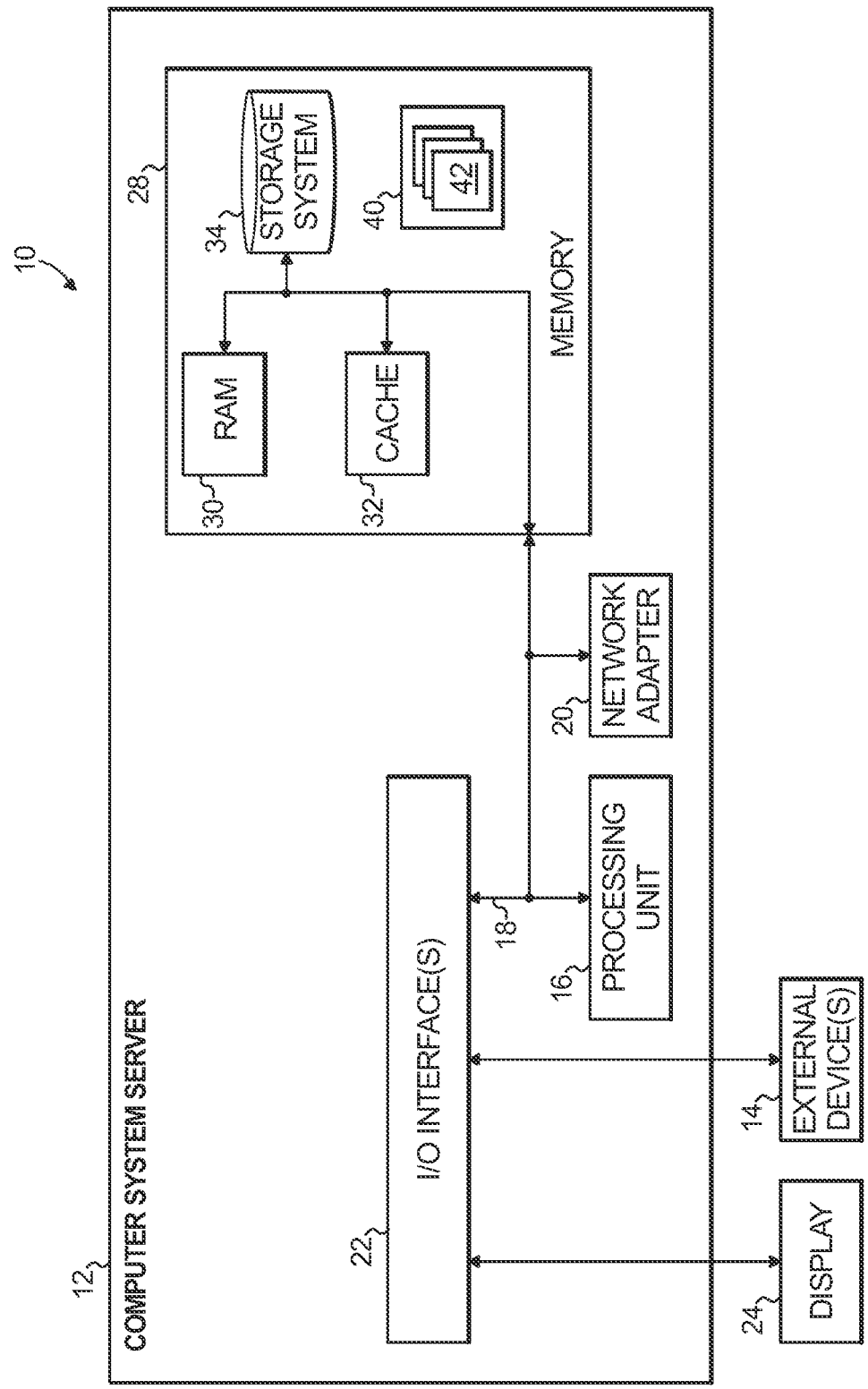
FIG. 41 depicts a cloud computing node according to an embodiment of the present invention.

Referring now to FIG. 41, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Figure 42:
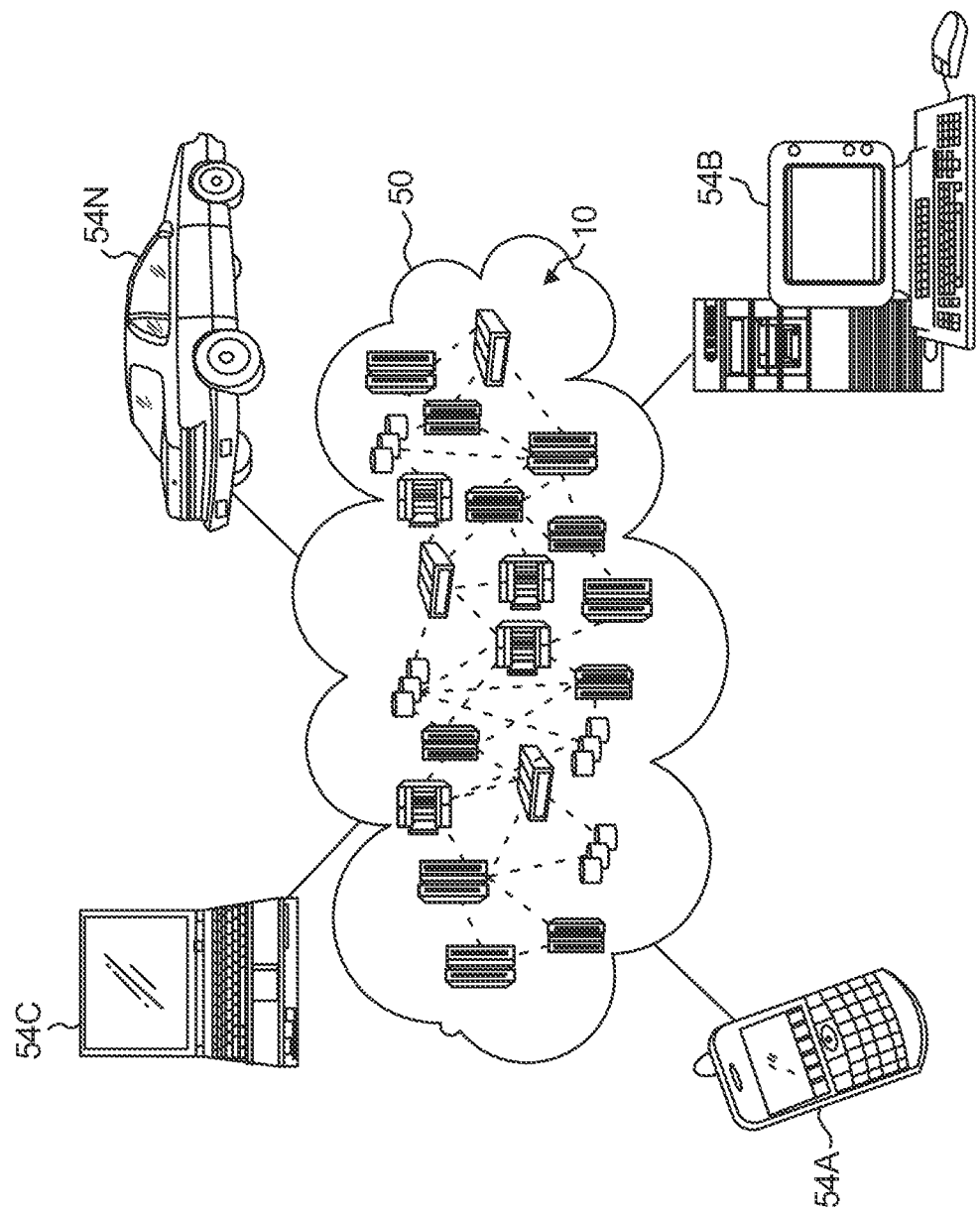
FIG. 42 depicts a cloud computing environment according to an embodiment of the present invention.

Referring now to FIG. 42, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 42 are intended to be illustrative only and that computing nodes 10 and cloud computing environment 50 can communicate with any type of computerized device over any type of network and/or network addressable connection (e.g., using a web browser).

Figure 43:
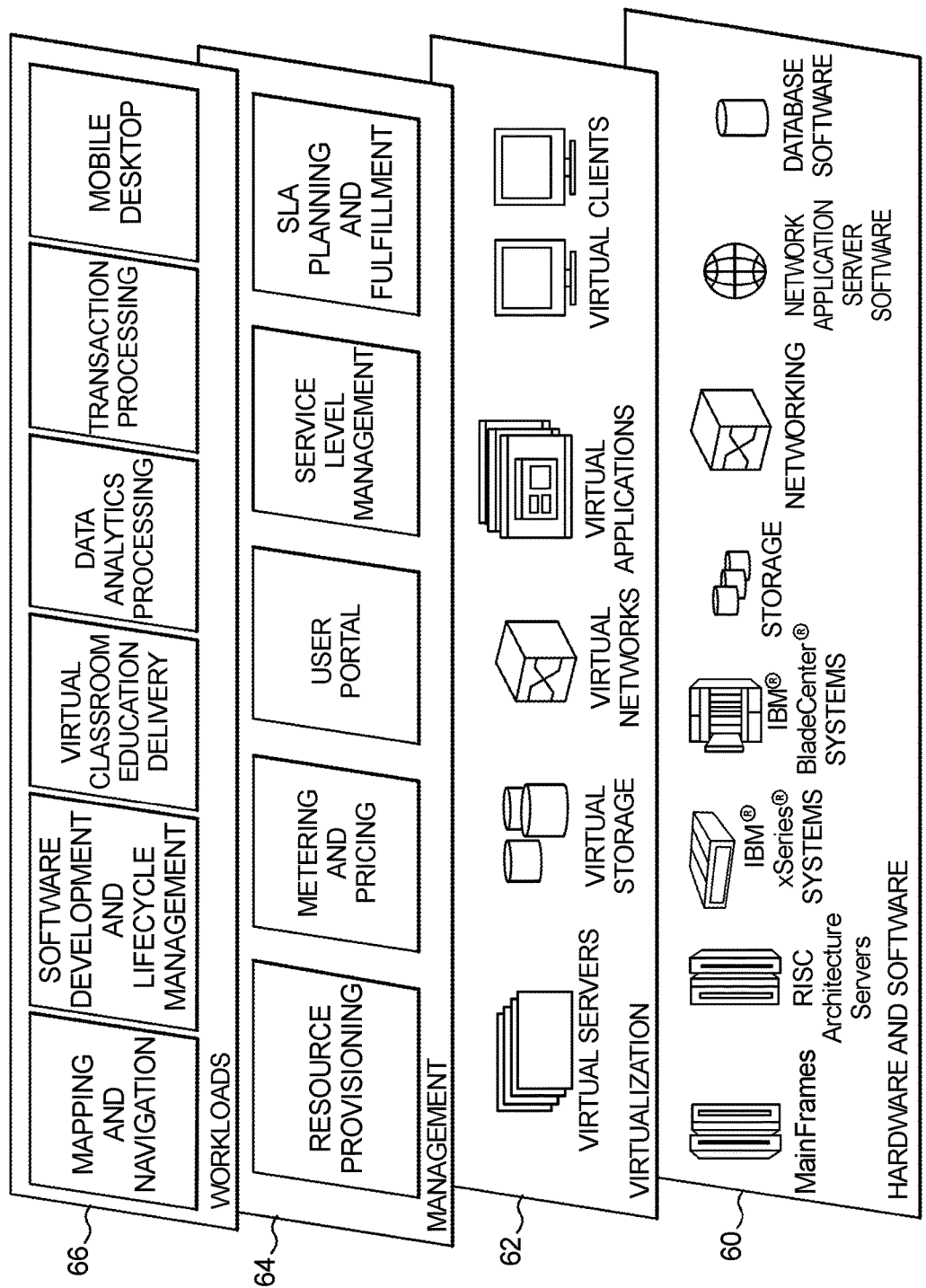
FIG. 43 depicts abstraction model layers according to an embodiment of the present invention.

Referring now to FIG. 43, a set of functional abstraction layers provided by cloud computing environment 50 (FIG. 42) is shown. It should be understood in advance that the components, layers, and functions shown in FIG. 43 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM Web Sphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provides pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing; and mobile desktop, as well as data aggregation and analysis over several analyses, to obtain, for example, geographical disease distribution and outbreaks patterns, as discussed above.

Recapitulation

Given the discussion thus far, it will be appreciated that, in general terms, an exemplary assembly is provided for interfacing with a microfluidic chip 238, 1616, 1618 having at least one microscopic channel configured to receive a liquid sample for analysis, at least one electrode embedded in the channel (e.g., at 969 and 3109), and at least one chip contact 1615, 1617 coupled to the at least one embedded electrode (for example, for dielectrophoresis, electro-osmosis, electro-wetting and/or liquid impedance detection). The assembly includes a chip carrier, which in turn includes a base (not separately numbered in FIG. 4) and a cover 240, cooperatively defining, with the base, a cavity 236 configured and dimensioned to receive the microfluidic chip 238. The cover is attachable to the base (e.g., already attached such as by hinge 252 or separate but capable of being attached by snapping or other suitable technique), to secure the microfluidic chip in the cavity of the base. The cover has an aperture 244 to permit the microscopic channel of the microfluidic chip to receive the sample for analysis and/or to permit passage of excitation and emission radiation. Also provided is at least one chip carrier contact to engage the at least one chip contact.

The assembly further includes an electronics module 110, which in turn includes at least one electronics module contact that engages the at least one chip carrier contact (e.g. flex cable 248); and a signal generator 112, coupled to the at least one electronics module contact, which applies (e.g. time multiplexing) at least one electrokinetic signal to the at least one embedded electrodes.

Please note that in many cases there will be a plurality of electrodes and a corresponding plurality of all the contacts. The signal generator will then selectively apply (e.g. time multiplexing) a plurality of electrokinetic signals to the plurality of embedded electrodes.

In a non-limiting example, the embedded electrodes are dielectrophoresis electrodes, and the electrokinetic signals are dielectrophoresis signals.

The assembly even further includes an optical module 118, which in turn includes an excitation radiation source 120, which causes excitation radiation to impinge on the sample through the aperture; and an emission radiation detector 124 which detects radiation emitted from the sample through the aperture. The assembly still further includes a mechanical module 102 including a chip-carrier receiving structure (see, e.g., FIG. 11—1107) relatable with respect to the optical module for focus and at least one degree of translational freedom. The mechanical module is electrically coupled to the electronics module. The focus and the at least one degree of translational freedom are controlled by the electronics module via the electrical coupling.

At least some embodiments further include a signal processing module 126, electrically coupled to the emission radiation detector 124, which processes a signal indicative of the radiation emitted from the sample through the aperture for communication to an operator. Communications can be wired and/or wireless. The signal processing module can be integrated with the electronics module or stand-alone.

In at least some cases, the cavity 236 configured and dimensioned to receive the microfluidic chip 238 is formed in the base of the chip carrier; and the plurality of chip carrier contacts 234 are formed on the cover of the chip carrier.

In at least some cases, the cover of the chip carrier is secured to the base of the chip carrier with at least one hinge 252 and a secure mechanism 242. The cover of the chip carrier has a side which faces the base of the chip carrier, and which is provided, in some instances, with a hydrophobic cushion layer 246 to avoid contamination.

As seen, for example, in FIG. 11, some embodiments further include a housing 1101. The electronics module and the optical module can be located in the housing, and wherein the housing is formed with a region to receive the chip carrier 1107.

As seen for example in FIG. 7, in some instances, the electronics module is located in the chip carrier and the optical module is located in the housing, and the housing is formed with a region to receive the chip carrier.

As seen for example in FIG. 9, in some instances, the electronics module is located in the base of the chip carrier and the optical module is located in the cover of the chip carrier.

Some claims recite the chip as a workpiece in the preamble but do not explicitly claim it, while other claims additionally claim the microfluidic chip, which can be located in the cavity configured and dimensioned to receive the microfluidic chip.

In at least some cases, the at least one microscopic channel is sized to cause flow of the liquid sample by capillary action (e.g., capillary pump 3105).

In some cases, the at least one microscopic channel is formed with a loading pad region (seen under dropper at 250), and the at least one microscopic channel, the loading pad region, and the plurality of dielectrophoresis electrodes are collocated on a first side of the chip which faces the optical module 118. The plurality of chip contacts can also be located on the first side of the chip, and in some instances, are formed as a high density connector array. Such an array could be arranged, by way of example and not limitation, in at least one row of contacts in an area less than 100 square millimeters; in one specific non-limiting example, three rows of seven contacts in an area 4 millimeters by 9.4 millimeters, as seen in FIG. 19.

For the avoidance of doubt, the values in the previous paragraph are exemplary and non-limiting. Other embodiments do not necessarily have an upper area limit for the connectors, since the chip area is also not limited in one or more embodiments, except to keep costs reasonable. Internal arrangement of the microfluidics channels and the capillary pump could also be modified in some instances to free up space.

In some cases, the optical module further includes a mirror and lens assembly 1203 moveable with respect to the excitation radiation source, and the chip-carrier receiving structure is relatable with respect to the optical module for the focus and the at least one degree of translational freedom by keeping the chip-carrier receiving structure still and moving the mirror and lens assembly.

In another aspect, referring to FIG. 31, an exemplary method is provided for carrying out a test on a microfluidic chip having at least one microscopic channel 3111 configured to receive a liquid sample for analysis (e.g., on a loading pad), at least one analytic electrode (see, e.g., exemplary pair of electrodes 3109, in an interdigitated layout; multiple electrode pairs could be used for DEP purposes in other embodiments) embedded in the channel, a plurality of liquid-presence-sensing electrodes embedded in the channel, and a plurality of chip contacts 3103 coupled to the at least one analytic electrode and the plurality of liquid-presence-sensing electrodes. The method includes step 3119, detecting loading of the liquid sample, on a first such microfluidic chip, based on an impedance change at one of the liquid-presence-sensing electrodes. A further step 3121 includes, responsive to detecting the sample loading, on the first such microfluidic chip, starting a timer. An even further step 3137 includes, responsive to an impedance change at at least another one of the liquid-presence-sensing electrodes (as at 3123), when the timer has advanced past a first threshold but has not advanced past a second threshold (as at 3125, 3131), commencing application of electrokinetic signals to the at least one embedded analytic electrode Please note that the at least one embedded analytic electrode could be one of the liquid-presence-sensing electrodes or could be separate and distinct from the liquid-presence-sensing electrodes. Dedicated electrode pairs could be used for liquid position detection or the same pair of electrodes could be used for DEP (or other analysis) and liquid position detection. Thus, the at least one embedded analytic electrode could, but need not, be a dielectrophoresis electrode, and the electrokinetic signals could, but need not, be dielectrophoresis signals.

Referring to the encircled "5" in FIG. 31 as well as the capillary pump 3105 and decision block 3139, note that there is a pair of electrodes 3199 to detect capacity variation inside the capillary pump. The reason to continue the liquid monitoring (check for impedance change at 3139) is to ensure that the liquid continues to flow. To simplify, liquid presence measurements are undertaken at the beginning (at the loading pad 3113 see encircled "2" and decision block 3119), in the beginning (see encircled "3" and decision block 3119, electrodes 3107) and in the end of the capillary pump (see encircled "5" and decision block 3139, electrodes 3199).

In some cases, the method includes repeating the detecting and starting steps for another liquid sample on another chip when chips are not reusable, and, responsive to an impedance change at the at least another one of the embedded electrodes, when the timer has not advanced past the first threshold, outputting an error signal to indicate at least one of potential leakage and low flow resistance (NO branch of 3131 to 3133).

In some cases, the method includes repeating the detecting and starting steps for another liquid sample on another chip when chips are not reusable, and, responsive to no impedance change at the at least another one of the embedded electrodes prior to the timer advancing past the second threshold, outputting an error signal to indicate at least one of potential clogging, bubble formation, and high flow resistance (NO branches of 3123, 3125 to 3127).

Aspects of one or more embodiments of the invention, or elements thereof, can be implemented in the form of an apparatus including a memory and at least one processor that is coupled to the memory and operative to perform exemplary method steps (e.g., smart phone, cloud server).

One or more embodiments can make use of software running on a general purpose computer or workstation. With reference to FIG. 41, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 41) running a server program. It will be understood that such a physical server may or may not include a display and keyboard.

One or more embodiments can be at least partially implemented in the context of a cloud or virtual machine environment, although this is exemplary and non-limiting. Reference is made back to FIGS. 41-43 and accompanying text.

It should be noted that any of the methods described herein can include an additional step of providing a system comprising distinct software modules embodied on a computer readable storage medium. The method steps can then be carried out using the distinct software modules and/or sub-modules of the system, executing on one or more hardware processors such as 16. Further, a computer program product can include a computer-readable storage medium with code adapted to be implemented to carry out one or more method steps described herein, including the provision of the system with the distinct software modules.

One example of user interface is hypertext markup language (HTML) code served out by a server or the like, to a browser of a computing device of a user (e.g., "smart" phone). The HTML is parsed by the browser on the user's computing device to create a graphical user interface (GUI).

Exemplary System and Article of Manufacture Details

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An assembly for interfacing with a microfluidic chip having at least one microscopic channel configured to receive a liquid sample for analysis, at least one electrode embedded in the at least one microscopic channel, and at least one chip contact coupled to the at least one embedded electrode, said assembly comprising:
    a chip carrier, in turn comprising:
        a base;
        a cover, cooperatively defining, with said base, a cavity configured and dimensioned to receive the microfluidic chip, said cover being attachable to said base, to secure the microfluidic chip in said cavity of said base, said cover having an aperture to permit the microscopic channel of the microfluidic chip to receive the sample for analysis and to permit passage of excitation and emission radiation; and
        at least one chip carrier contact to engage the at least one chip contact;
    an electronics module, in turn comprising:
        at least one electronics module contact that engages the at least one chip carrier contact;
        a signal generator, coupled to said at least one electronics module contact, which applies at least one electrokinetic signal to said at least one embedded electrode;
    an optical module, in turn comprising;
        an excitation radiation source which causes excitation radiation to impinge on the sample through said aperture; and
        an emission radiation detector which detects radiation emitted from the sample through said aperture; and
    a mechanical module comprising a chip-carrier receiving structure, relatable with respect to said optical module for focus and at least one degree of translational freedom, said mechanical module being electrically coupled to said electronics module, said focus and said at least one degree of translational freedom being controlled by said electronics module via said electrical coupling.

2. The assembly of claim 1, wherein there are a plurality of the electrodes embedded in the at least one microscopic channel, a plurality of the chip contacts coupled to the plurality of embedded electrodes, a plurality of said chip carrier contacts to engage the plurality of chip contacts, a plurality of said electronics module contacts that engage said plurality of chip carrier contacts, and wherein said signal generator is coupled to said plurality of electronics module contacts to selectively apply a plurality of said electrokinetic signals to the plurality of embedded electrodes.

3. The assembly of claim 1, wherein the plurality of the electrodes embedded in the at least one microscopic channel comprise dielectrophoresis electrodes, and wherein said electrokinetic signals comprise di electrophoresis signals.

4. The assembly of claim 3, further comprising a signal processing module, electrically coupled to said emission radiation detector, which processes a signal indicative of said radiation emitted from the sample through said aperture for communication to an operator.

5. The assembly of claim 4, wherein:
    said cavity configured and dimensioned to receive the microfluidic chip is formed in said base of said chip carrier; and
    said plurality of chip carrier contacts are formed on said cover of said chip carrier.

6. The assembly of claim 5, wherein said cover of said chip carrier is secured to said base of said chip carrier with at least one hinge.

7. The assembly of claim 6, wherein said cover of said chip carrier has a side which faces said base of said chip carrier, and which is provided with a hydrophobic cushion layer.

8. The assembly of claim 3, further comprising a housing, wherein said electronics module and said optical module are located in said housing, and wherein said housing is formed with a region to receive said chip carrier.

9. The assembly of claim 3, further comprising a housing, wherein said electronics module is located in said chip carrier and said optical module is located in said housing, and wherein said housing is formed with a region to receive said chip carrier.

10. The assembly of claim 3, wherein said electronics module is located in said base of said chip carrier and said optical module is located in said cover of said chip carrier.

11. The assembly of claim 3, further comprising said microfluidic chip, located in said cavity configured and dimensioned to receive said microfluidic chip.

12. The assembly of claim 11, wherein said at least one microscopic channel is sized to cause flow of said liquid sample by capillary action.

13. The assembly of claim 12, wherein said at least one microscopic channel is formed with a loading pad region, and wherein said at least one microscopic channel, said loading pad region, and said dielectrophoresis electrodes are collocated on a first side of said chip which faces said optical module.

14. The assembly of claim 13, wherein said plurality of chip contacts are also located on said first side of said chip.

15. The assembly of claim 13, wherein said plurality of chip contacts are formed as a high density connector array arranged in at least one row of contacts in an area less than 100 square millimeters.

16. The assembly of claim 15, wherein said plurality of chip contacts formed as said high density connector array are arranged in three rows of seven contacts in an area 4 millimeters by 9.4 millimeters.

17. The assembly of claim 3, wherein:
said optical module further comprises a mirror and lens assembly moveable with respect to said excitation radiation source; and
said chip-carrier receiving structure is relatable with respect to said optical module for said focus and said at least one degree of translational freedom by keeping said chip-carrier receiving structure still and moving said mirror and lens assembly.

\* \* \* \* \*